US012655460B2

(12) United States Patent     (10) Patent No.: US 12,655,460 B2
Kirby et al.     (45) Date of Patent: Jun. 16, 2026

(54) RAPID ANTIMICROBIAL SUSCEPTIBILITY TESTING BY IMAGE ANALYSIS

(71) Applicant: Beth Israel Deaconess Medical Center, Inc., Boston, MA (US)

(72) Inventors: James E. Kirby, Weston, MA (US); Ramy Arnaout, Chestnut Hill, MA (US); Kenneth P. Smith, Somerville, MA (US); Matthew Ware, Merrimack, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 798 days.

(21) Appl. No.: 17/765,328

(22) PCT Filed: Sep. 28, 2020

(86) PCT No.: PCT/US2020/053030
§ 371 (c)(1),
(2) Date: Mar. 30, 2022

(87) PCT Pub. No.: WO2021/067170
PCT Pub. Date: Apr. 8, 2021

(65) Prior Publication Data
US 2022/0340952 A1     Oct. 27, 2022

Related U.S. Application Data

(60) Provisional application No. 62/908,912, filed on Oct. 1, 2019.

(51) Int. Cl.
*C12Q 1/18*     (2006.01)
*G01N 35/00*     (2006.01)
(Continued)

(52) U.S. Cl.
CPC ............. *C12Q 1/18* (2013.01); *G01N 35/028* (2013.01); *G01N 35/10* (2013.01); *G06T 7/0012* (2013.01);
(Continued)

(58) Field of Classification Search
None
See application file for complete search history.

(56) References Cited

U.S. PATENT DOCUMENTS 6,372,485 B1   4/2002   Clark et al.
9,809,842 B2 * 11/2017   Bouzid ................ H04N 1/1017
(Continued)

FOREIGN PATENT DOCUMENTS

DE   10 2009 023 279    12/2010
WO   2017/218202    12/2017
WO   2018136864 A1   7/2018

OTHER PUBLICATIONS

Grimes, Sally E. "A basic laboratory manual for the small-scale production and testing of I-2 Newcastle disease vaccine." RAP publication 22 (2002): 76-79. (Year: 2002).*
(Continued)

*Primary Examiner* — Matthew C Bella
*Assistant Examiner* — Johnny B Duong
(74) *Attorney, Agent, or Firm* — Kilpatrick Townsend & Stockton LLP

(57) ABSTRACT

Embodiments allow for rapid antimicrobial susceptibility testing (AST) at a low cost. Embodiments may use changes in the pixel intensity from reflected light to determine microorganism growth and antimicrobial resistance. Dilutions of an antimicrobial are added to a standard well plate or other array. A pathogen or other microorganism may be added to the dilutions in the well plate. The well plate may be incubated for a time period less than 3 hours. The well
(Continued)

plate may then be imaged and the resulting image data may be analyzed. Wells where the microorganism is able to grow may appear darker than wells where the microorganism did not grow. Differences pixel intensity of the wells is used to determine the susceptibility or resistance of the microorganism to the antimicrobial. The image data may be used to determine the minimum inhibitory concentration (MIC), the lowest dilution concentration of antimicrobial that inhibits growth.

32 Claims, 11 Drawing Sheets

(51) Int. Cl.

| | | |
|---|---|---|
| *G01N 35/02* | (2006.01) | |
| *G01N 35/10* | (2006.01) | |
| *G06T 7/00* | (2017.01) | |
| *H04N 23/56* | (2023.01) | |

(52) U.S. Cl.
CPC ... *H04N 23/56* (2023.01); *G01N 2035/00356* (2013.01); *G06T 2207/20081* (2013.01); *G06T 2207/30072* (2013.01)

(56) References Cited

U.S. PATENT DOCUMENTS

| | | | | |
|---|---|---|---|---|
| 11,834,696 | B2 * | 12/2023 | Tao | G01N 15/06 |
| 2003/0040032 | A1 * | 2/2003 | DeMarsh | C12Q 1/18 |
| | | | | 435/32 |
| 2007/0216906 | A1 | 9/2007 | Javidi et al. | |
| 2014/0278136 | A1 | 9/2014 | Shamsheyeva et al. | |
| 2016/0010138 | A1 | 1/2016 | Shamsheyeva et al. | |
| 2017/0191020 | A1 | 7/2017 | Recht et al. | |
| 2018/0010084 | A1 | 1/2018 | Uematsu et al. | |
| 2019/0203252 | A1 | 7/2019 | Ashby et al. | |
| 2019/0249128 | A1 | 8/2019 | Wikswo et al. | |
| 2021/0130868 | A1 * | 5/2021 | Tao | G16H 50/20 |
| 2021/0332320 | A1 * | 10/2021 | Sei | G01N 21/253 |

OTHER PUBLICATIONS

Walker, David. Comparing the Depth of Field of Two Types of Flatbed Scanner, a CIS and a CCD Model. The Wayback Machine—https://web.archive.org/web/20130122213052/http://www.microscopy-uk.org.uk/mag/artjan13/dw-scanner-type.html. 2013 (Year: 2013).*

Gorocs, Zoltan, and Aydogan Ozcan. "Biomedical imaging and sensing using flatbed scanners." Lab on a Chip 14.17 (2014): 3248-3257. (Year: 2014).*

Miller, Ingrid, Johanne Crawford, and Elisabetta Gianazza. "Protein stains for proteomic applications: which, when, why ?." Proteomics 6.20 (2006): 5385-5408. (Year: 2006).*

Ray. Scanning Halftone Images. https://web.archive.org/web/20190909161540/http://brisray.com:80/computers/halftone.htm. Archived Oct. 9, 2019. (Year: 2019).*

Application No. EP20871284.4 , Extended European Search Report, Mailed On Dec. 21, 2023, 8 pages.

"MicroScan, Walkway Instrument Guide", Beckman Coulter, Apr. 2018, 202 pages.

Rahman et al. "Evaluation of a scanner-assisted colorimetric MIC method for susceptibility 12 testing of gram-negative fermentative bacteria." Applied and Environmental Microbiology, vol. 70, No. 4, Apr. 2004, p. 2398-2403. Retrieved on Mar. 29, 2022 from <https://aem.asm.org/content/aem/70/4/2398.full.pdf>.

Smith et al. "Development of MAST: a microscopy-based antimicrobial susceptibility testing platform." SLAS Technology, 2017, vol. 22(6), pp. 662-674, Aug. 24, 2017.

Stroustrup, et al., "The C. elegans Lifespan Machine", Nat. Methods, Jul. 2013, pp. 665-670. Doi: 10.1035/nmeth.2475, https://www.ncbi.nlm.nih.gov/pmc/articles/PMC3865717/.

International Application No. PCT/US2020/053030 received an International Search Report and Written Opinion, mailed Aug. 2, 2021, 19 pages.

* cited by examiner

Incubates at 37C          Scanner takes timepoints          Image file output 305          310          315

410

No growth

405

Growth

800

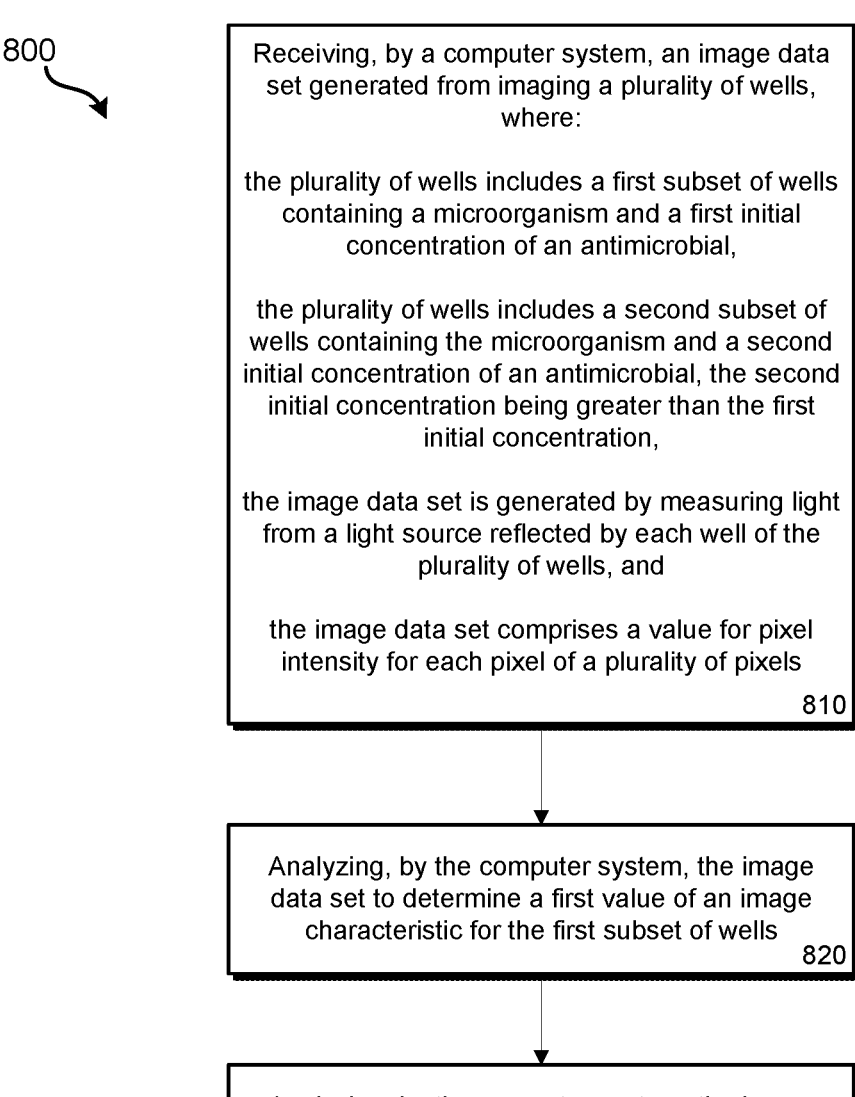

Receiving, by a computer system, an image data set generated from imaging a plurality of wells, where:

the plurality of wells includes a first subset of wells containing a microorganism and a first initial concentration of an antimicrobial, the plurality of wells includes a second subset of wells containing the microorganism and a second initial concentration of an antimicrobial, the second initial concentration being greater than the first initial concentration, the image data set is generated by measuring light from a light source reflected by each well of the plurality of wells, and the image data set comprises a value for pixel intensity for each pixel of a plurality of pixels

810

Analyzing, by the computer system, the image data set to determine a first value of an image characteristic for the first subset of wells

820

Analyzing, by the computer system, the image data set to determine a second value of the image characteristic for the second subset of wells

830

Determining a classification of the resistance of the microorganism to the antimicrobial using at least one of the first value or the second value

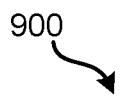

900

Receiving an input data structure, the input data structure including:
an input image data set including a value for pixel intensity for each pixel of a sample plurality of pixels, the image data set generated from imaging a sample plurality of wells, the sample plurality of wells containing a sample microorganism and a plurality of initial concentrations of an antimicrobial, and
a sample map representing the sample plurality of wells with values indicating an initial concentration of the antimicrobial in each well
910

Inputting the input data structure into a model, the model trained by:                                                          920

Receiving a first plurality of first data structures, each first data structure of the plurality of first data structures including:
a first image data set including a value for pixel intensity for each pixel of a first plurality of pixels, the first image data set generated from imaging a first plurality of wells, the first plurality of wells containing a first microorganism and the plurality of initial concentrations of the antimicrobial, the first microorganism having a known minimum inhibitory concentration to the antimicrobial, and
a first map representing the first plurality of wells with values indicating the initial concentration of the antimicrobial for each well                                                          930

Storing a plurality of first training samples, each including one of the first plurality of first data structures and a first label indicating the known minimum inhibitory concentration of the first microorganism to the antimicrobial          940

Optimizing, using the plurality of first training samples, parameters of the model based on outputs of the model matching or not matching corresponding labels of the first labels when the first plurality of first data structures is input to the model                                                          950

Determining, using the model, the minimum inhibitory concentration of the sample microorganism to the antimicrobial
960

FIG. 9

RAPID ANTIMICROBIAL SUSCEPTIBILITY TESTING BY IMAGE ANALYSIS

CROSS REFERENCES TO RELATED APPLICATIONS

This application is a 371 National Stage filing of PCT Application No. PCT/US2020/053030, filed Sep. 28, 2020, which claims the benefit of priority to U.S. Provisional Patent Application No. 62/908,912 filed Oct. 1, 2019, the contents of which are hereby incorporated by reference in their entirety for all purposes.

STATEMENT REGARDING FEDERALLY SPONSORED RESEARCH OR DEVELOPMENT

This invention was made with government support under Grant No. AI130434 awarded by the National Institutes of Health. The government has certain rights in the invention.

BACKGROUND

There has been a dramatic emergence of multidrug-resistant Enterobacteriaceae (Center for Disease Dynamics Economics and Policy. 2015. State of the World's Antibi-otics, 2015. CDDEP, Washington, DC). In a survey of short- and long-term acute care hospitals in the United States, 17.8% and 3.6% of Enterobacteriaceae causing central line bloodstream infections, catheter-associated urinary tract infections, and surgical site infections were extended-spec-trum~-lactam resistant and carbapenem resistant, respec-tively (Weiner et al., *MMWR* 65:235-241 (2016)). Limited therapeutic options remain to treat these and other multi drug-resistant pathogens, including other Gram-negative rods, Gram-positive cocci, Gram positive rods, and Gram-negative cocci, and practical availability of remaining active agents may be further limited by associated drug toxicities or patient allergies. Accordingly, there remains a critical need to test antimicrobials not available in pre-made panels or supplementary FDA-cleared methods.

Conventional methods used in clinical laboratories world-wide require isolation of bacteria on culture plates as single bacterial colonies. The colonies are then used to set up one of several methods (the broth microdilution reference method, agar dilution, disk diffusion, gradient diffusion, or several commercial methods that are either modified ver-sions of the broth microdilution method, provided by instru-ments such as Becton Dickinson's Phoenix, Fisher Scien-tific's Senstitre, or Siemens's Microscan) or extrapolate the results from the broth microdilution method based on growth kinetics of organisms in culture (e.g. Biomerieux's Vitek 2). Usually available testing is limited to first-line drugs. In practice, these methods provide antimicrobial susceptibility testing (AST) results in a minimum of two days after specimen receipt in the clinical lab: at least one day to isolate pure bacterial colonies, and one additional day to obtain the AST results from these colonies. With emerging antimicrobial resistance, this two-or-more day delay may lead to adverse clinical outcomes.

Systems that provide faster AST results from pure bacte-rial colonies are extremely expensive. Some machines cost over $100,000 and would still take seven or more hours to run after isolating a pure bacterial colony. The cost of testing a sample can be $200 or more. As a result of their high cost, rapid AST systems would not likely be widely available throughout the world, including in rural areas and develop-ing countries.

Thus, there is a need to develop rapid and affordable antimicrobial testing systems and methods. These and other issues are addressed by embodiments of the present inven-tion.

SUMMARY

Embodiments of the present invention allow for rapid antimicrobial susceptibility testing (AST) at a low cost. Embodiments may use changes in the pixel intensity from reflected light to determine microorganism growth and anti-microbial resistance. Doubling dilutions or other set of concentrations of an antimicrobial are added to a standard well plate or other ordered or disordered array. A pathogen or other microorganism may be added to the doubling dilutions in the well plate. The well plate may be incubated for a time period less than 3 hours, faster than other technologies. The well plate may then be imaged and the resulting image data may be analyzed. Wells where the microorganism is able to grow may appear darker or lighter than wells where the microorganism did not grow. The different pixel intensity of the wells is used to determine the resistance of the microorganism to the antimicrobial. The image data may be used to determine the minimum inhibi-tory concentration (MIC), the lowest doubling-dilution or other concentration of antimicrobial that inhibits growth.

The hardware used in embodiments of the present inven-tion may involve components similar to those mass-pro-duced for commercially available equipment, such as stan-dard well plates, inkjet printers, and flatbed scanners. The systems may not require specialized reagents for analysis. As a result of the availability of components, embodiments of the present invention may be cost effective.

A better understanding of the nature and advantages of embodiments of the present invention may be gained with reference to the following detailed description and the accompanying drawings.

BRIEF DESCRIPTION OF THE DRAWINGS

A further understanding of the nature and advantages of various embodiments may be realized by reference to the following figures. In the appended figures, similar compo-nents or features may have the same reference label. Further, various components of the same type may be distinguished by following the reference label by a dash and a second label that distinguishes among the similar components. If only the first reference label is used in the specification, the descrip-tion is applicable to any one of the similar components having the same first reference label irrespective of the second reference label.

FIG. 8 shows a method for testing antimicrobial susceptibility according to embodiments of the present invention.

FIG. 9 shows a method for testing antimicrobial susceptibility according to embodiments of the present invention.

TERMS

Figure 1:
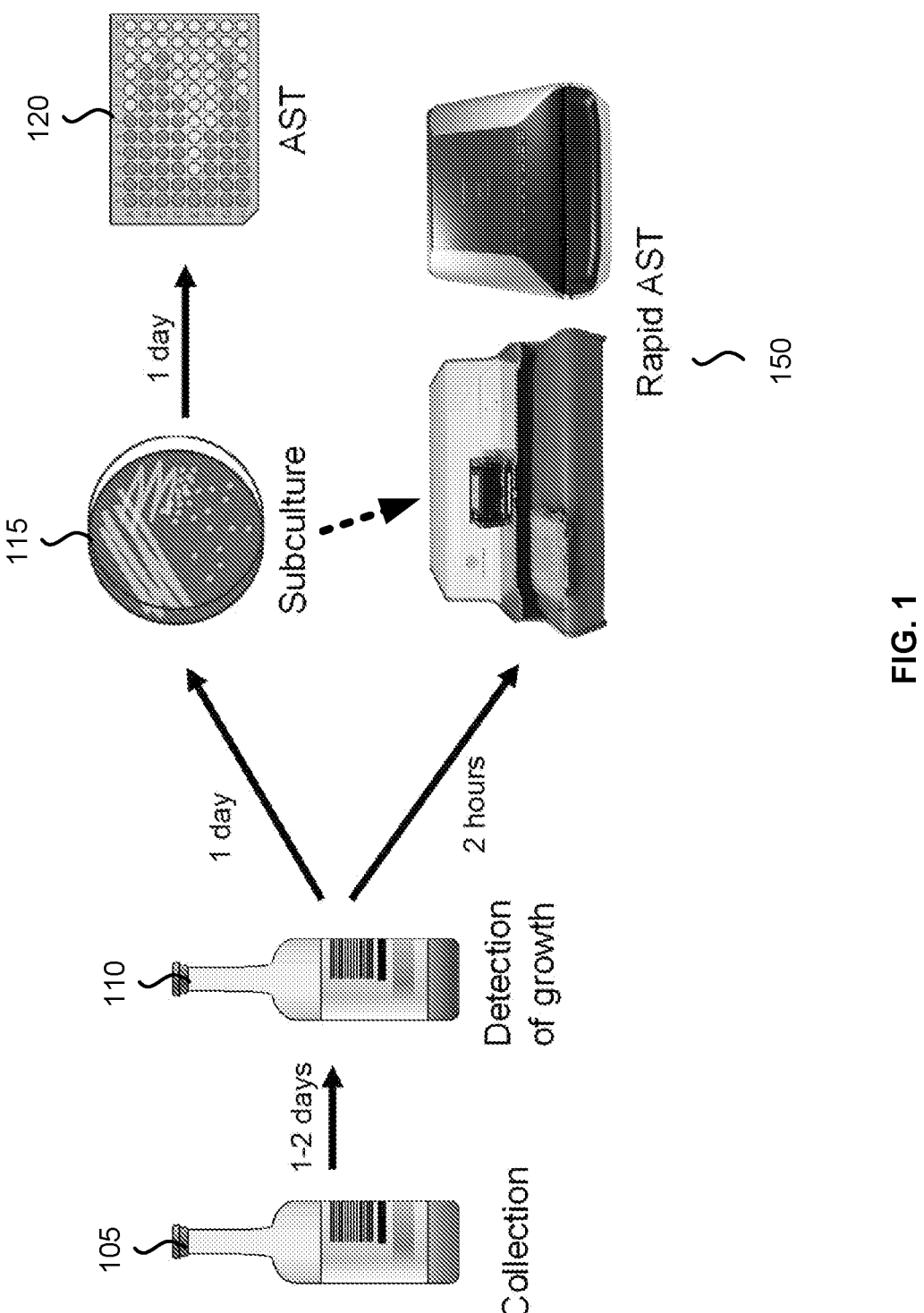
FIG. 1 shows process flows for conventional AST and rapid AST embodiments of the present invention.

As used herein, the terms "media," "medium," "broth," "culture broth," and the like all refer to a nutrient mixture suitable to culture a desired cell or microorganism.

As used herein, the term "microorganism" refers to a member of one of following classes: bacteria, fungi, algae, and protozoa, and can also include, for purposes of the present disclosure, viruses, prions, or other pathogens. In various embodiments, bacteria, viruses, and in particular, human and animal pathogens, are evaluated. It will be understood by practitioners in the art that the exact composition of a growth medium will be dictated by the cell or microorganism type to be dispensed, cultured, and assayed.

In particular embodiments, a culture medium can comprise one or more of water, proteins, amino acids, caesein hydrolysate, salts, lipids, carbohydrates, salts, minerals, and pH buffers. A culture medium may also contain extracts such as meat extract, yeast extract, tryptone, phytone, peptone, and malt extract.

Exemplary cell culture media include, without limitation, balanced salt solutions, nutrient mixtures, basal media, complex media, serum free media, insect cell media, virus production media, serum, fetal bovine serum, serum replacements, antibiotics, antimycotics, blood components other than serum, supplements including but not limited to nicotinamide adenine dinucleotide, hemin, hematin, pyridoxal; or Isovitalex; and lysed horse or sheep blood, or any combination thereof. The culture medium can be a commercially available culture medium such as, for example, cation-adjusted Mueller-Hinton broth (available from Becton Dickinson and other suppliers); cation-adjusted Mueller-Hinton broth with 2.5-5% laked horse blood; cation-adjusted Mueller-Hinton broth supplemented with Isovitalex or equivalent; RPMI 1640 with 0.2% glucose; *Hemophilus* test medium broth; Brain heart infusion broth; and Middlebrook 7H9 Broth (for mycobacteria). In some cases, RPMI 1640 is adjusted to pH of 7.0 and buffered with 0.165 mol/L MOPS (3-[N-morpholino] propanesulfonic acid) for analysis of yeast.

As used herein, "antimicrobials" and "antimicrobial agents" include antibiotics (also termed antibacterial) and anti-fungal, anti-viral, and anti-parasitic agents. Also encompassed in the terms "antimicrobial" and "antimicrobial agents" are antimicrobial antibodies (e.g., antibodies that bind to and directly kill organisms or enhance their clearance during infection), antimicrobial peptides, phages, phage lysins (e.g., bacteriophage endolysins, which are phage-encoded peptidoglycan hydrolases able to cause lysis of cells such as bacteria), anti-virulence compounds (e.g., anti-toxins that interfere with bacterial disease progression by binding to target proteins produced during infection or anti-adhesins that interfere with bacteria binding to tissue), and other alternative class or non-standard agents developed as therapeutic agents for treating infections caused by one or more microbial organisms. Exemplary anti-virulence compounds are described by Totsika, *Curr Med Chem.* 2016 February; 6(1): 30-37. No current AST platforms are able to test these alternative or non-standard antimicrobial agents singly or in combination.

Exemplary classes of antimicrobial agents include, without limitation, aminoglycosides (e.g., gentamicin, tobramycin, amikacin, netilmicin, apramycin, spectinomycin), carbapenems (e.g., ertapenem, imipenem, meropenem, doripenem), first and second generation cephalosporins (e.g., cefazolin, cefuroxime), third and fourth generation cephalosporins (e.g., cefotaxime or ceftriaxone, ceftazidime, cefepime); cephalosporins β-lactamase inhibitor combinations (e.g. ceftazidime-avibactam, ceftolozane-tazobactam); fluoroquinolones (e.g., ciprofloxacin, moxafloxacin, levofloxacin), anti-MRSA cephalosporins (e.g., ceftaroline), glycopeptides (e.g., vancomycin), tetracyclines (e.g., tetracycline, doxycycline, minocycline), penicillins (e.g., ampicillin-sulbactam, amoxicillin-clavulanic acid, nafcillin, piperacillin/tazobactam), monobactams (e.g., aztreonam), macrolides and ketolides (e.g., azithromyin, clarithromycin); lincosamides (e.g., clindamyin); oxazolidinones (e.g., linezolid, tedizolid); glycylcyclines (e.g., tigecycline); antifolates (e.g., trimethoprim/sulfamethoxazole): nucleoside analogue inhibitors (e.g., azidothymidine); RNA polymerase inhibitors (e.g., rifampicin); anti-mycobacterial agents (e.g., isoniazide, pyrizinamide, ethambutol, capreomycin, bedaquiline, pretomanid); polymyxins (e.g., colistin, polymyxin B); lipoglycopeptides (e.g., oritavancin, telavancin and dalbavancin); phenicols (e.g., chloramphenicol), lipopeptides (e.g., daptomycin); antifungals (e.g., amphotericin; azoles such as fluconazole, posaconazole, voriconazole; and echinocandins such as caspofungin, micafungin; and terbenafine and flucytosine); anti-viral agents (e.g., azidothymidine, lamivudine, acyclovir, ganciclovir, valganciclovir, cidofivir, efavirenz, oseltamivir, raltegravir, zanamivir, peramivir, adamantane antivirals (e.g., amantadine, rimantadine), foscarnet, brincidofovir, famciclovir, valacyclovir, neuraminidase inhibitors, protease inhibitors, integrase strand transfer inhibitors); antimicrobial peptides (e.g., POL7080, Polyphor, Ltd.); antimicrobial antibodies (e.g., Salvecin (AR-301), Aerumab, MEDI3902_Aerucin); phages (e.g., AB-SAO1 from AmpliPhi); and lysins (e.g., CF-3101, Contract Corp.; N-Rephasin, Intron Biotechnology). Antimicrobial antibodies in clinical development are described in Pew Charitable Trusts, "A Scientific Roadmap for Antibiotic Discovery," available at pewtrusts.org/~/media/assets/2016/05/ascientificroadmapforantibioticdiscovery.pdf.

A "biological sample" refers to any sample that is taken from a subject (e.g., a human, such as a patient having an infection, suspected of having an infection, or at risk of having an infection). The biological sample can be a tissue biopsy, a fine needle aspirate, a bodily fluid, such as blood, plasma, serum, urine, vaginal fluid, fluid from a hydrocele (e.g. of the testis), vaginal flushing fluids, pleural fluid, ascitic fluid, cerebral spinal fluid, pericardial fluid, saliva, sweat, tears, sputum, bronchoalveolar lavage fluid, discharge fluid from the nipple, aspiration fluid from different parts of the body (e.g. thyroid, breast), etc. Stool samples can also be used. Sputum after liquifaction with N-acetylcysteine may also be used.

The term "classification" as used herein refers to any number(s) or other characters(s) that are associated with a particular property of a sample. For example, a "+" symbol (or the word "positive") could signify that a pathogen is susceptible to a concentration of antimicrobial. The classification can be binary (e.g., positive or negative) or have more levels of classification (e.g., a scale from 1 to 10 or 0 to 1).

The terms "cutoff" and "threshold" refer to predetermined numbers used in an operation. For example, a cutoff value can refer to a value above which image characteristic values are excluded. A threshold value may be a value above or below which a particular classification applies. Either of these terms can be used in either of these contexts. A cutoff or threshold may be "a reference value" or derived from a reference value that is representative of a particular classification or discriminates between two or more classifications. Such a reference value can be determined in various ways, as will be appreciated by the skilled person. For example, metrics can be determined for two different cohorts of subjects with different known classifications, and a reference value can be selected as representative of one classification (e.g., a mean) or a value that is between two clusters of the metrics (e.g., chosen to obtain a desired sensitivity and specificity). As another example, a reference value can be determined based on statistical analyses or simulations of samples.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term "about" or "approximately" can mean within an order of magnitude, within 5-fold, and more preferably within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

DETAILED DESCRIPTION

Embodiments of the present invention allow rapid determination of antimicrobial susceptibility testing (AST) for microorganisms, including human pathogens. Conventional AST methods result in a minimum of two days after specimen receipt to obtain AST results, with one day for isolating pure bacterial colonies, and one additional day to obtain the AST results from the colonies.

With emerging antimicrobial resistance, a two-day delay or any delay may lead to adverse clinical outcomes. Specifically, when patients are suspected of having an infection, they are placed on empiric therapy: our best guess as to what the antibiotic will effectively treat the infecting pathogen. Generally broad-spectrum antibiotics are given with the hopes of covering any potential pathogen. Once the AST results are available, directed therapy, tailored to the susceptibility profile of the pathogen, can be given. However, there are at least three problems with the current empiric-to-directed therapy approach.

First, the pathogen may be resistant to the empiric therapy, meaning empiric therapy may not be effective. This is increasingly a problem, given the epidemic spread of antimicrobial resistance. Especially in severe infections, it is known that delay in starting effective therapy can lead to significant morbidity and mortality. For example, for *Pseudomonas aeruginosa* bloodstream infections, which are particularly dangerous, every additional day's delay before the start of effective therapy is associated with a 10% increase in mortality.

Second, for multidrug-resistant pathogens in particular, conventional AST results may show that all first-line agents tested in the clinical laboratory are ineffective. This requires testing additional agents, leading to further delays. Some of this testing may have to be performed at outside laboratories. For example, agents of last resort, such as colistin, can only be tested at present by reference techniques, which are beyond the capability of most clinical labs. In all, this means that for the most resistant isolates, there may be a delay of up to a week before the appropriate active therapies are determined.

Third, empiric therapy is by definition broad spectrum. Broad-spectrum agents destroy our normal flora, regardless of whether they are effective or not against the infecting pathogen. Destruction of normal flora leads to loss of what is called colonization resistance. Patients in a hospital setting can then become colonized with highly resistant flora. This includes, for example, Clostridiodies (*Clostridium*) *difficile* and *Candida* species. Patients may then develop very serious diseases like *C. difficile* colitis and *Candida* bloodstream infections. The former may lead to severe colitis and death. The latter is associated with 30-50% attributable mortality. Therefore, the shortest time possible until a switch to directed therapy is highly desirable to spare normal flora and reduce the impact on colonization resistance.

AST may be used for bloodstream infections. Bloodstream infections are the most immediate life-threatening infections in the hospital setting. Bloodstream infection implies loss of local source control and spread of the infecting organisms throughout the body.

FIG. 1 shows process flows for conventional AST and rapid AST embodiments of the present invention. A blood specimen is easy to collect. For example, a blood specimen may be obtained with a blood draw from a patient using a syringe. Specifically, a blood specimen does not require surgery or invasive procedures to obtain. However the number of organisms is low and may be on the order of <1-10 colony-forming units per milliliter of blood. Therefore, when we collect blood specimens from patients, we must first culture the blood to increase the number of organisms, in order to allow further analysis such as AST.

Blood is collected into blood culture bottles for this purpose at the patient bedside. Bottle 105 is a bottle after blood collection. Generally, a blood culture draw consists of a set of bottles, an aerobic bottle and an anaerobic bottle. The bottles may be used for different pathogens. These bottles foster the growth of aerobic and facultative anaerobic, and anaerobic bacterial organisms, respectively. The bottles also may grow yeast. There is a separate type of bottle that will grow pathogenic fungi and mycobacteria. Blood cultures are a very high-volume process: for example, at BIDMC, we process approximately 40,000 blood culture sets per year from patients with suspected bloodstream infections, approximately 5-10% of which flag as positive on our commercial blood culture system. We use the Becton Dickinson BACTEC FX blood culture system. There are several competing systems used in clinical labs, all of which may operate on similar principles: detection of organisms' metabolism.

Bottle 110 shows a bottle after detection of growth. When a blood culture bottle 110 flags positive, the system alerts technologists to undertake further steps in order to guide clinicians in use of appropriate therapy. Detection of growth may occur 1-2 days after collection. A positive culture typically has ~$10^9$ organisms per ml, reflecting logarithmic growth of organisms initially inoculated from the sample into the bottle. From the standard aerobic and anaerobic blood cultures sets, technologists perform a Gram stain and plate the blood-culture broth to isolate colonies. Dish 115 shows a plate after the Gram stain and isolating colonies. Isolating colonies may take 1 day or more after detection of growth. Isolated colonies will then be used for AST 120. AST may take an additional day after subculture. Therefore, from the time a blood culture bottle becomes positive there is a two-or-more day delay in obtaining AST results that allow a switch from empiric to appropriate/effective narrower spectrum therapy.

I. Overview

The technology described in this disclosure reduces the time from positive blood culture to AST results from two-or-more days to less than 3 hours, with our preliminary results indicating accurate results in 1.5 hours. With further refinement we expect to reduce this time even further, including down to 30 minutes. Consequently, we expect this invention will have significant impact on patient care.

A. Current Systems

Embodiments of the present invention provide faster AST results at a lower cost than recently commercially available technologies. One example of a commercial AST system is the FDA-cleared Accelerate Diagnostics Phenosense system. This system takes positive blood-culture broth, electrophoretically immobilizes organisms onto a solid surface, and then microscopically follows growth of organisms into colonies. However, the Phenosense will only provide AST results after 7 hours. The technology extrapolates the AST readout from testing a single concentration of each antibiotic. In other systems, such as the Vitek, which extrapolates AST from a minimum of 2-3 concentrations. Such extrapolations may often be associated with an unacceptable rate of error, especially for multidrug-resistant organisms for which correct AST results are critical.

A major limitation of the Accelerate Phenosense system is that it can test only one pathogen on one system at a time. Another limitation is that each assay cartridge costs more than $200. A third is that each assay system platform, the machine on which the assays are run, costs ~$100,000. A typical reasonably sized hospital system would require several such systems to address the many positive blood cultures each day, as the lab could not wait for 7 hours until starting each successive positive blood culture test (which would defeat the purpose of a "rapid" AST system). So a laboratory may need a capital investment of ≥$300,000 to employ such as system, with a very high per-test reagent cost. Furthermore, the Accelerate system at present is only approved for positive blood culture broth detection. Potential future use for higher volume microbiology laboratory testing at more than $200 per sample with low throughout is extremely problematic.

B. AST in Less than 3 Hours

In contrast, embodiments of the present invention will allow us to test any antimicrobial agent at any desired concentration, for many agents and concentrations, at will. FIG. 1 shows that Rapid AST 150 embodiments can be done in two hours, without the subculture. Nevertheless, Rapid AST 150 could still be used after subculture from dish 115. Currently, we are testing true two-fold serial dilutions (also called doubling dilutions) of antimicrobials, as is performed in the reference AST method, to allow us to accurately determine the minimal inhibitory concentration, or MIC. MIC is lowest doubling-dilution concentration of antibiotic that inhibits growth. The MIC is an important and discriminatory data from AST. It is a phenotypic measure that predicts patient response to therapy. In reference AST format, it is performed by testing the effects of doubling dilutions of antibiotics on the growth of a pathogen inoculated into a standard growth medium called cation adjusted Mueller-Hinton broth. In current standard of care, growth inhibition is interpreted typically after 16-20 hours of incubation at 35° C.

Embodiments of the present invention, based on the foundation of the doubling dilution MIC method, will require significantly less extrapolation than methods like Accelerate or Vitek. Specifically, the AST plates in embodiments of the present invention, if incubated for the time performed in reference methods would approximate the reference method. However, embodiments of the present invention allow reference broth susceptibility testing panels to be read much more quickly: less than 3 hours currently, with anticipated improvements.

Figure 2:
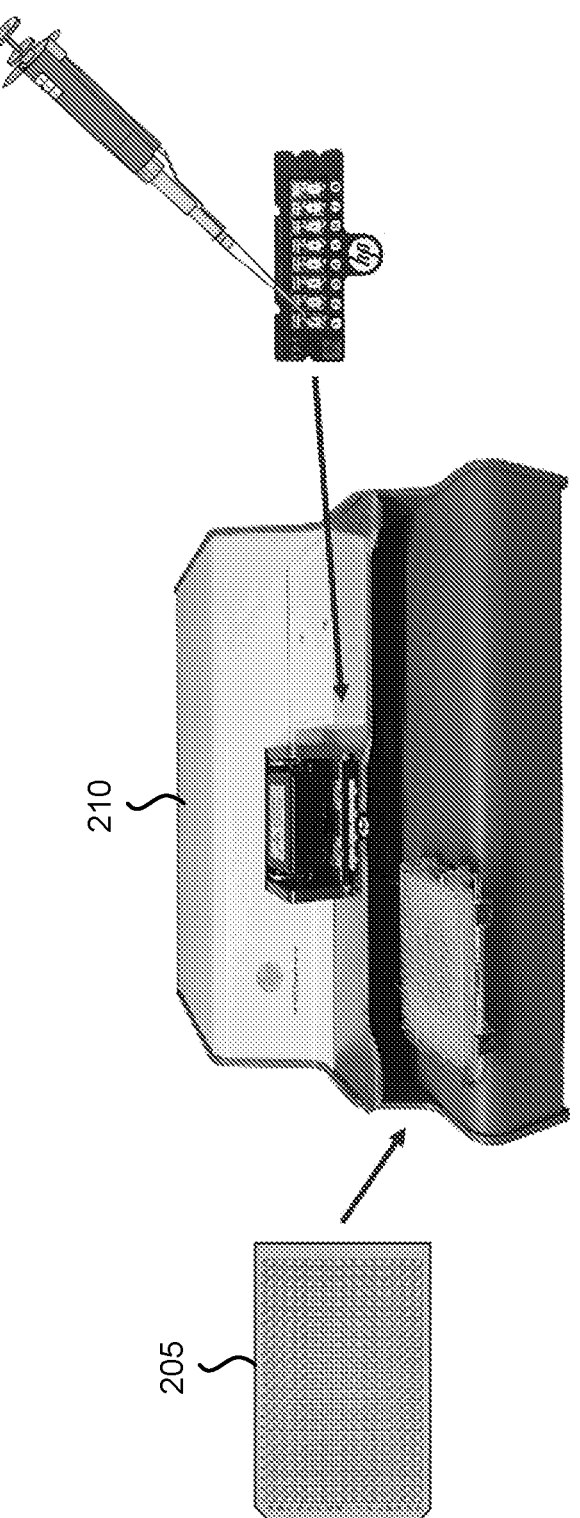
FIG. 2 shows a diagram of the dispensing technology according to embodiments of the present invention.

FIG. 2 shows a diagram of the dispensing technology. The dispensing technology may use well plate 205, which may be a standard 96-, 384-, or 1536-well microtiter plate. Well plate 205 contains doubling dilutions of antimicrobials. Any antimicrobials can be used. Antibiotics are mentioned as an example of an antimicrobial, but any antimicrobial or other treatment agent (e.g. antifungal, antiviral, anti-parasitic) can be used unless context clearly dictates otherwise. The doubling dilution series can be prepared at the time of use, or plates with doubling dilutions can be pre-made and stored with lyophilized antibiotics or with antibiotics in broth that are frozen and thawed before use. In embodiments, 50 μl of broth are added to wells in well plate 205 and desired two-fold dilutions of antibiotics are added to wells using inkjet printing technology 210 as described in WO 2017/218202 A1, the entire contents of which are incorporated by reference for all purposes. In other embodiments, antibiotics can be added either manually or with any of several suitable liquid handling devices. Positive blood culture broth is then added to the microtiter wells. The positive blood culture broth or dilutions of the positive blood culture broth can be added to the wells using any of several liquid handling devices or manually or through use of an inkjet printer 210 which we determined can quantitatively print out positive blood culture broth.

Typically positive blood-culture broth has organisms at $5×10^9$ colony-forming units per mL. In our experiments, we determined that this could be diluted 5-fold in sterile water and 0.3% tween-20 and this dilution dispensed at 250 nl per well to create a starting inoculum of approximately $2.5×10^7$ per mL in wells in a 384 well plate containing a volume of 10 μl. Surfactant such as Tween-20 can be added to facilitate inkjet printing to rapidly distribute bacteria to each well of a 384-well plate or other liquid handling devices known to the field can be similarly used. The final inoculum can be varied in the range of $10^3$ per ml to $10^8$ per ml to optimize performance of rapid AST depending on the application, organism, and incubation temperature.

Figure 3:
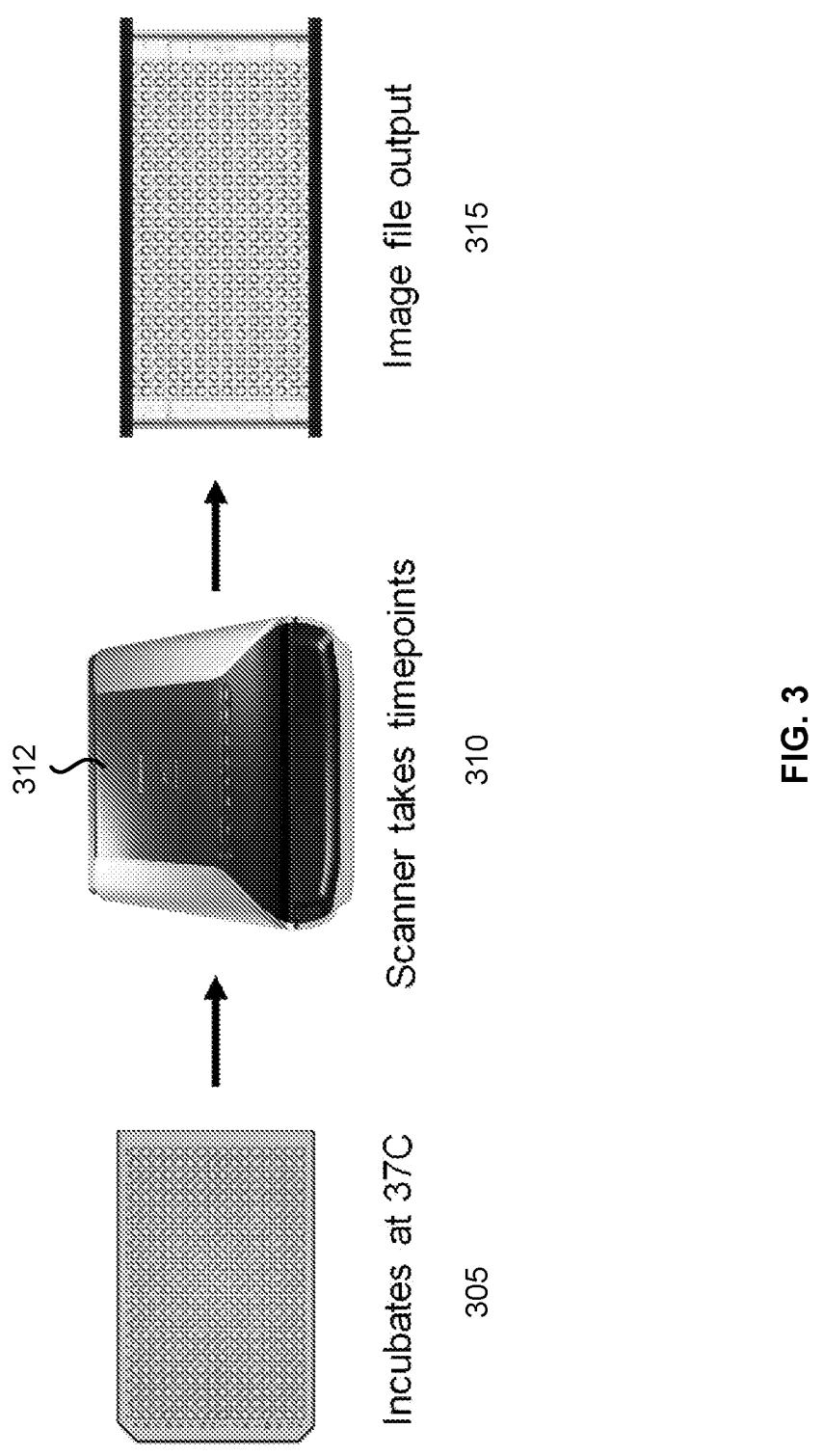
FIG. 3 illustrates operations after the well plate is pre-pared according to embodiments of the present invention.

FIG. 3 illustrates operations after the well plate is prepared. The microtiter plate is then placed in an incubator. The temperature of the incubator can be set at any temperature from 15° C. to 72° C. to optimize growth of organisms for different applications. Typically temperatures for bacterial pathogen testing will be in the range of 35° C. to 37° C.

Block 305 shows that the well plate is incubated at 37° C. Either continually or at specific time points, the plate is scanned at block 310 using a scanning technology such is found in a flatbed scanner 312. Scanner 312 may consist of a linear charge-coupled device (CCD) sensor, contact image sensor (CIS), or photomultiplier tube sensor that is at least the diameter of the plate if the sensor is in linear format and the sensor scans across the plate or the size of the plate if a single image of the plate is captured simultaneously. Scanning results in an image file output 315.

Figure 4B:
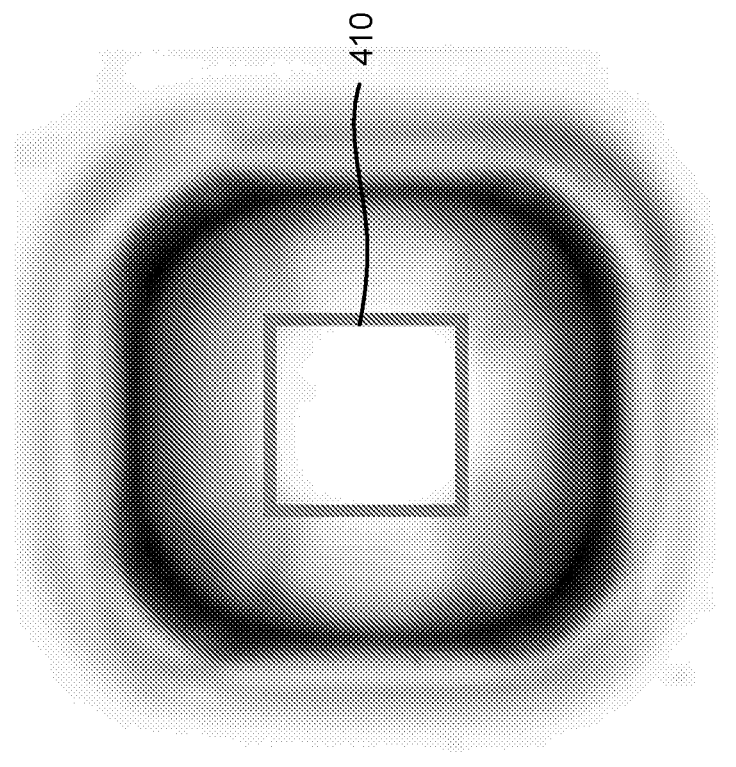
FIG. 4B shows an image of a well without microorganism growth according to embodiments of the present invention.
Figure 4A:
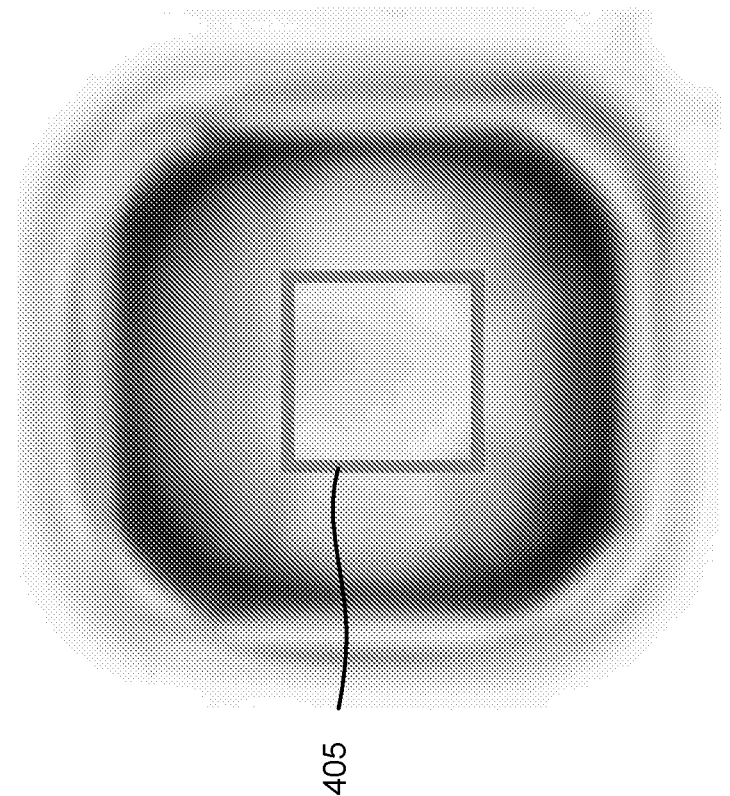
FIG. 4A shows an image of a well with microorganism growth according to embodiments of the present invention.

FIG. 4A shows an image of a well with microorganism growth. FIG. 4B shows an image of a well without microorganism growth. Portion 405 and portion 410 of the images align with the center portion of a well. Portion 405 is visually darker than portion 410. While this difference can be noticed by the naked eye, most images of wells with growth are not visually discernible from a well without growth by a person and may need to be analyzed by a computer. Portion 405 and portion 410 exclude pixels from outside the center portion of the well. The areas outside portion 405 and portion 410 include the sidewalls of the well, which do not contain the testing sample with the microorganism, broth, and antimicrobial. Areas within the well itself are obscured by shadowing and other distortions from the imaging process. Moreover, image distortions may vary depending on the location of the well in the plate.

Custom placement of biological replicates of doubling dilutions on a given plate—a custom platemap—are used to further control for artifacts and positional variance. Raw images of the plates in standard imaging formats such as TIFF or PNG are processed to correct for per-timepoint, per-axis-per-plate, and per-scan variability and then compared to detect differences in pixel intensities that indicate growth of the bacteria, resulting in data that can be represented in two-dimensional plots of doubling-dilution concentration (x-axis) vs. growth (y-axis).

We have made use of a CCD flatbed scanner to scan plates. In our example, the plates are incubated in a separate incubator and placed on a plate bed scanner at different time points for reading. Using a flatbed scanner, we have determined that accurate AST results can be obtained with incubation times of 1.5 hours or less. We have shown that the combination of appropriately designed platemaps and the above image processing steps substantially decrease the time to determination of MICs, specifically accurately determining MICs at 3 hours, with preliminary data showing MICs in many cases down to 1.5 hours, and machine learning on each time series and higher CCD resolution suggesting still further improvements.

C. Features

Embodiments of the present invention include key advantages over other AST technologies.

A first advantage is speed. The current clinical standard is AST in 16-20 hours. Embodiments of the present invention can perform AST at 3 hours, with preliminary data down to 1.5 hours. This short time needed for AST was unexpected, particularly in view of the inexpensive hardware used for AST.

A second advantage is using inexpensive standard technologies. Embodiments of the present invention can use a standard mid-2000s-era flatbed scanner, which can be obtained at a cost of ~$200 or less. Complex robotics and moving parts are not needed for imaging. As a result, manufacturing costs may be low.

A third advantage is having inexpensive consumables. Our technology uses the 96-, 384-, and 1,536-well microtiter plates that are standard across biological research and clinical practice and available inexpensively from multiple manufacturers (Corning, Eppendorf, Fisher, Nunc, etc.). Our broth may be the clinical standard. Expensive reagent supplements are not needed. For example, the broth does not require lanthanide-series metals or moieties as tags to identify organism surface area or mass.

A fourth advantage is versatility. Embodiments of the present invention may allow for continuous measurement. Embodiments do not require addition of a reagent and are not limited to being an end-point assay (once the assay is performed, measurements cannot be continued). Embodiments of the present invention work well from direct-from-colony AST as well as direct-from-blood-culture AST.

II. Example Results

The pixel intensity from imaged wells can be used in determining the relative growth of a microorganism. We conducted experiments to demonstrate that MIC can be determined with the dispensing, imaging, and analysis methods and systems described herein.

A. Results Using Gentamicin

Figure 5:
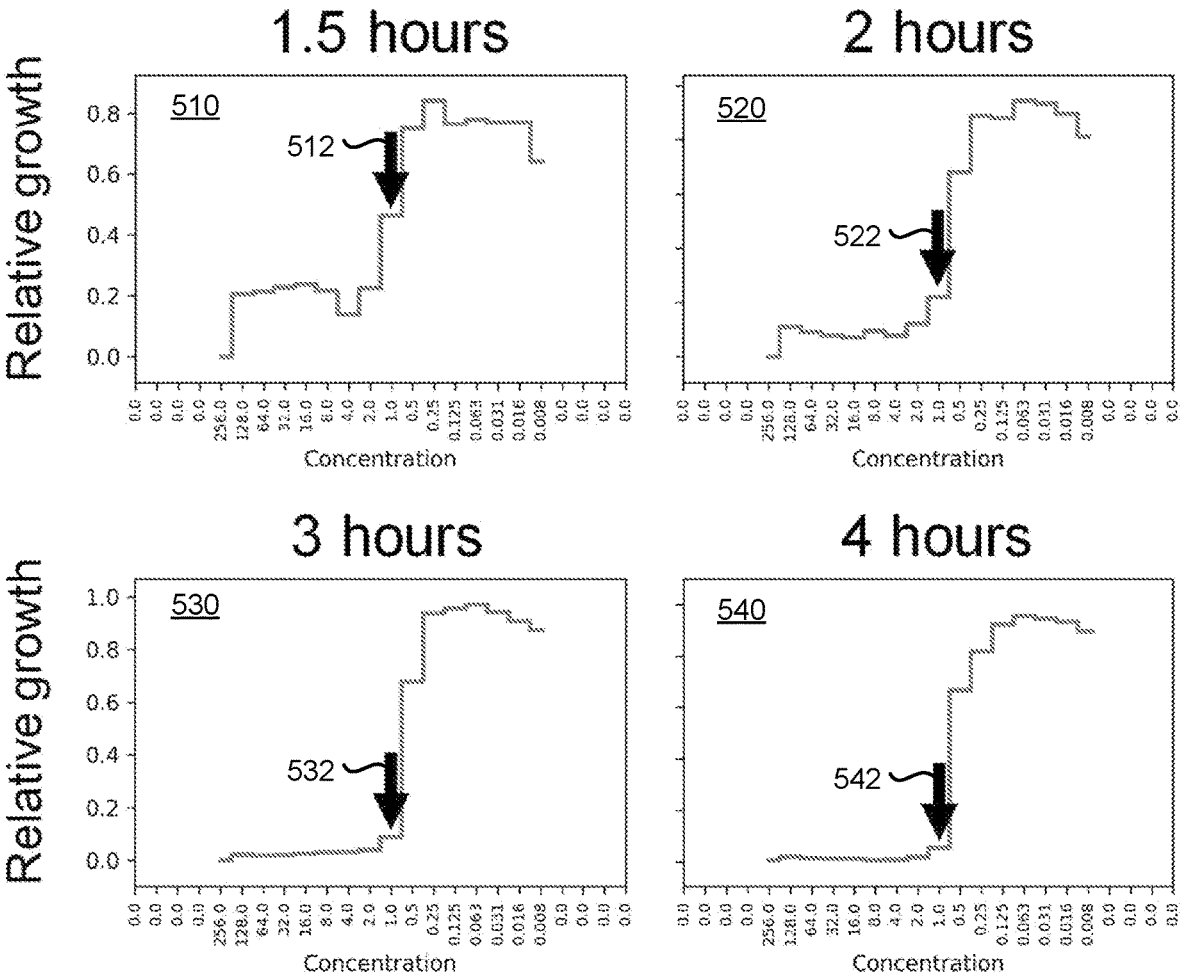
FIG. 5 shows graphs resulting from data from imaging using a flatbed scanner to image well plates according to embodiments of the present invention.

FIG. 5 shows graphs resulting from data from imaging using a flatbed scanner well plates. A microorganism (*E. coli*) was added to dilutions of gentamicin in a well plate. The well plate was incubated at 37° C. and scanned at various times. The well plate was physically moved from the incubator and then placed back in the incubator at several times. Because of this movement, the well plate was not in the exact same position on the scanner at each scan.

The graphs in FIG. 5 plot relative growth, as determined using pixel intensity, versus concentration of gentamicin in μg/μl. The largest concentration of gentamicin is shown on the left-most side of each graph, and the smallest concentration of gentamicin is shown on the right-side of each graph.

Graph 510 shows results after 1.5 hours of incubation. Graph 520 shows results after 2 hours of incubation. Graph 530 shows results after 3 hours of incubation. Graph 540 shows results after 4 hours of incubation.

Graph 510 shows a graph that has an increase in the relative growth of the microorganism at gentamicin concentrations at or below 0.5 μg/μl. The relative growth is greater than at concentrations at or above 1.0 μg/μl. The relative growth at 1.0 μg/μl is between the relative growth at 0.5 μg/μl and 1.0 μg/μl. The MIC could be determined to be either 0.5 μg/μl or 1.0 μg/μl from graph 510. Plus or minus one doubling dilution is considered within the allowable variance of the reference method. Arrow 512 indicates an MIC of 1.0 μg/μl. Arrows 522, 532, and 542 indicate the 1.0 μg/μl concentration for different periods of incubation. Graphs 510, 520, 530, and 540 all show similar responses. Graph 540 at 4 hours shows a clear increase in relative growth at concentrations at or below 0.5 μg/μl. The MIC in graphs 520, 530, and 540 may also be determined to be 1.0 μg/μl.

B. Results Using Cephalosporins

The imaging and analysis techniques may also be sensitive enough to capture unusual patterns of growth of microorganisms in the presence of antimicrobials. For example, cephalosporins, including cephalexin and cefepime, may cause cell filamentation. These filaments can be on the order of tens of microns in length, which is on the order of the resolution of the scanner used in these experiments.

Figure 6:
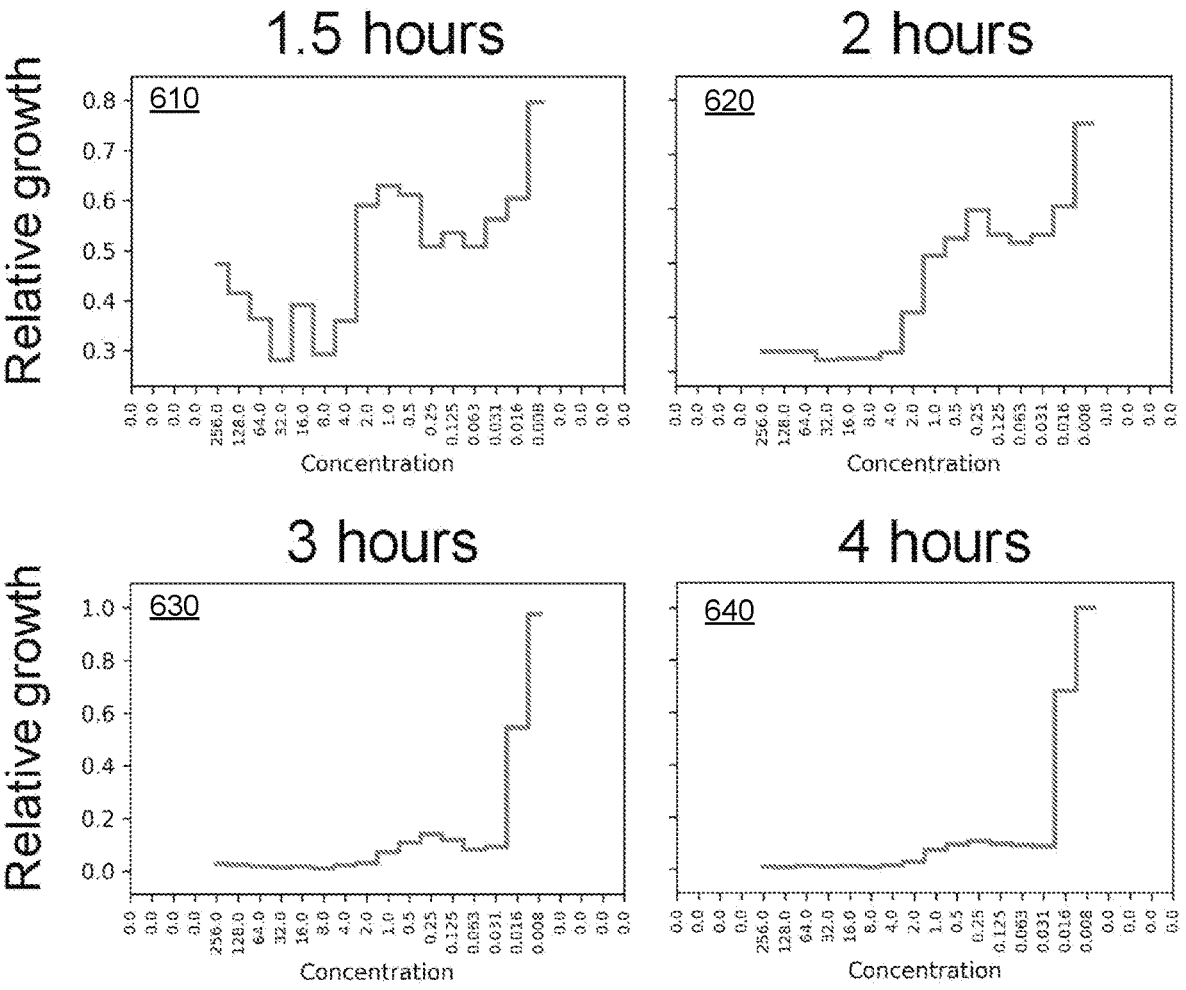
FIG. 6 shows graphs of resulting from data from imaging using a flatbed scanner well plates with dilutions of cefepime according to embodiments of the present inven-tion.

FIG. 6 shows graphs of resulting from data from imaging using a flatbed scanner to scan well plates with dilutions of cefepime. Graph 610 shows results after 1.5 hours of incubation. Graph 620 shows results after 2 hours of incubation. Graph 630 shows results after 3 hours of incubation. Graph 640 shows results after 4 hours of incubation. Graph 610 and graph 620 show relative growth that undergoes a decrease after an initial increase as concentrations of cefepime are reduced. This pattern may be capturing cell filamentation caused by the cefepime, which results in increased pixel intensity. Graph 630 and graph 640 do not show the decrease after the increase with lower cefepime concentrations. The MIC in graph 630 and graph 640 can be determined to be 0.031 μg/μl.

These cefepime results show that the scanning method can detect different growth patterns resulting from antimicrobials. Additionally, even with different growth patterns, the imaging method described herein may still determine the MIC in 3 hours.

C. Additional Results

Further experiments are run using the scanning image method using different microorganisms and different antimicrobials. Enterobacteriaceae, *Pseudomonas*, and *Acinetobacter* bacteria are tested with dilutions of meropenem, gentamicin, ciprofoxacin, and cefepime. Methicillin-sensitive *Staphylococcus aureus* (MSSA) is tested with dilutions of vanomycin, linezolid, daptomycin, and oxacillin. *Enterococcus* is tested with dilutions of vanomycin, linezolid, daptomycin, and ampicillin. MICs are determined at various incubation times. Machine learning using time series data may be applied to determine the MIC from an incubation time of under 1.5 hours, when the MIC is not readily apparent from data at 1.5 hours.

D. Improvements in Time for MIC

AST results are expected to be achieved in times less than the demonstrated 1.5 hours. Improvements may be seen from using a higher resolution sensor. Previous experiments used a 4800 dpi scanner. Scanners with 9600 dpi are commercially available and not cost prohibitive. A higher resolution scanner will allow for more pixels to be analyzed per well. A higher quality scanner may also reduce the distortions and shadowing in each well. More pixels may result in a better signal for growth. Machine learning models to filter out the pixels for analysis and machine learning models for determining MIC from image data may also reduce the duration of incubation needed. Additionally, additives may be added to the well that may aid image analysis. Additives may include a signal amplifier, a pH indicator, or a dye indicative of metabolism. A signal amplifier may include any of several systems in which detection of a change (e.g., pH change) sets off a cascade, chain reaction, or positive feedback loop of chemical reactions. For example, a fall in pH causes an inhibitor molecule to dissociate from an enzyme that produces a pigment.

III. Example System

Figure 7:
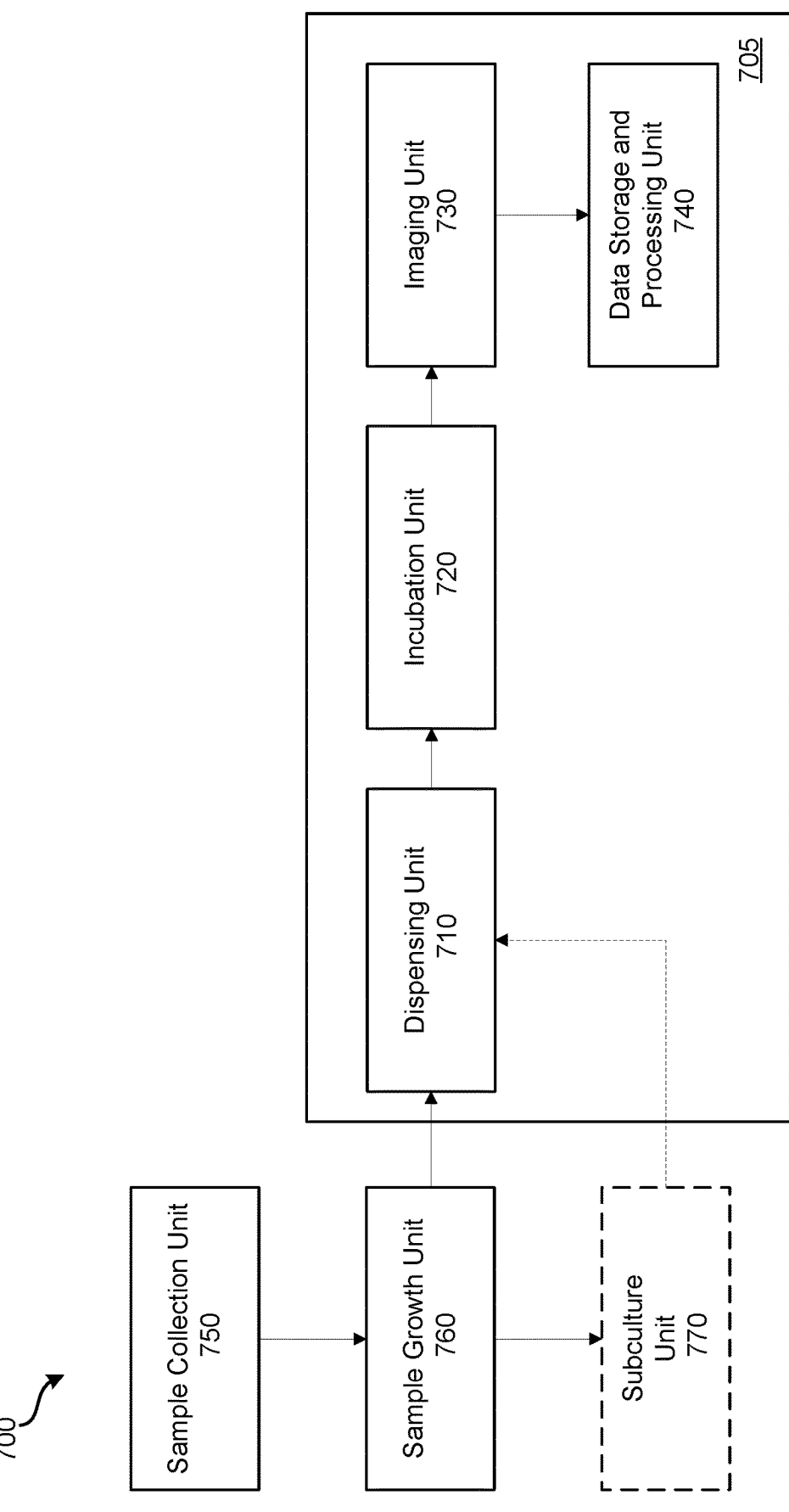
FIG. 7 shows a system for rapid AST according to embodiments of the present invention.

FIG. 7 shows a system 700 for rapid AST. System 700 may include a subsystem 705, which includes a dispensing unit 710, an incubation unit 720, an imaging unit 730, and a data storage and processing unit 740.

Dispensing unit 710 may be configured for automated dispensing of a microorganism or a plurality of concentrations of an antimicrobial to a plurality of locations on a well plate. The well plate may include 96 or more wells, including 384, 1,536, 3,456, or 9,600 wells. Each well may have a volume from 10 nl to 2 ml, including 0.1 to 0.3 ml or 0.03 to 0.1 ml. The wells may include polystyrene, polypropylene, or polycarbonate. The well plates may have a flat or substantially flat bottom. The well plates may not include lenses or other optical components that improve the imaging of a well. In some embodiments, a lens may be added to each well to improve imaging of the well. The plurality of concentrations may include serial dilutions of the antimicrobial. The plurality of locations on the well plate map to the wells of the well plate. In some embodiments, the well plate may be supplied with dilutions of an antimicrobial. The antimicrobials may be lyophilized or frozen until they are thawed for testing.

Dispensing unit 710 may be a dispensing unit described in WO 2017/218202 A1. The dispensing unit may dispense liquid using techniques and hardware used by an inkjet printer to dispense ink. Dispensing unit 710 may be configured for automated dispensing of a single concentration of microorganism to a plurality of wells in the well plate.

Incubation unit 720 may be configured to receive the well plate and to maintain a temperature set point. Incubation unit 720 may include a heater, a temperature sensor, a programmable controller, and insulated walls. Incubation unit 720 may be set at any temperature from 15° C. to 72° C., including 37° C. or any temperature described herein.

Imaging unit 730 may include a light source and a sensor. The imaging unit may be configured to measure light from the light source reflected by the well plate and to generate an image data set from the measured light. The sensor may have a resolution greater than or equal to 600 dpi, including from 600 to 1200 dpi, from 1200 to 4800 dpi, from 4800 to 9600 dpi, or greater than 9600 dpi. The sensor may be a charge-coupled device (CCD), contact image sensor (CIS), or photomultiplier tube sensor. The sensor may have bit depths of 24 or more, including 30 or more, 36 or more, or 48 or more.

The light source may include a fluorescent lamp or a xenon lamp. The light source may include a cold cathode fluorescent lamp. In some embodiments, the light source may be light emitting diodes (LEDs), and the sensor may be a CIS.

The light source may be configured to move, and imaging unit 730 may include a mirror or mirrors to reflect light to the sensor during movement of the light source. Light may pass through filters (e.g., for red, green, or blue) before the sensor so that a color image may be produced. The sensor, mirrors, and filter may be part of a scan head. The scan head may be moved by a motor (e.g., a stepper motor), so that all components of the scan head move simultaneously. The scan head may be attached to a stabilizer bar, and the scan head may be moved by a belt in communication with the motor. The scan head may move in one dimension only. In some embodiments, the scan head may move in two dimensions. The scan head may make only one pass across the well plate. In some embodiments, the scan head may make three passes across the well plate and may use a different color filter for each pass. An example of imaging unit 730 is a flatbed scanner. For example, the imaging unit may be Canon CanoScan 9000F MK II, which scans at 4800 dpi.

Imaging unit 730 may include a glass plate, on which the well plate sits during imaging. The well plate may be oriented such that the bottom of the well plate is closest to the sensor. In some embodiments, the well plate may be oriented so that the top of the well plate, and therefore the opening of each well, is closest to the sensor.

Imaging unit 730 may include a well plate holder to immobilize the well plate. The well plate holder may be a clamp, recessed portion of a surface to be imaged, a hinge, or other suitable device.

Data storage and processing unit 740 may include a processor configured to execute a plurality of instructions.

Data storage and processing unit may include logic system 2130, external memory 2140, and/or storage device 2145 in FIG. 10 or computer 10 in FIG. 11, all of which are described later. The processor may be configured to execute a plurality of instructions. The instructions may include analyzing the image data set to determine a first value of an image characteristic for a first subset of wells of the well plate, the first subset of wells having a first concentration of the microbial, analyzing the image data set to determine a second value of an image characteristic for a second subset of wells of the well plate, the first subset of wells having a second concentration of the microbial, the second concentration being greater than the first concentration, and determining a classification of the resistance of the microorganism to the antimicrobial using the first value and the second value. The plurality of instructions may include any method described herein.

Dispensing unit 710, incubation unit 720, imaging unit 730, and data storage processing unit 740 may be considered part of a subsystem 705. Subsystem 705 may include units after growth of the microorganism is detected in a biological sample.

System 700 may include a sample collection unit 750. Sample collection unit 750 may be configured to obtain a biological sample from a patient. The biological sample may be any described herein (e.g., a blood, urine, cerebral spinal, pleural fluid, pericardial fluid, bronchoalveolar lavage fluid, and sputum after liquifaction with N-acetylcysteine). In some embodiments, the sample is obtained by a medical practitioner with a syringe or other suitable device. The biological sample may be stored in a container, such as a bottle or vial.

System 700 may further include a sample growth unit 760. Sample growth unit 760 may be a blood culture system, including, for example, Becton Dickinson BACTEC FX blood culture system. With certain biological samples (e.g., urine, cerebral spinal fluid, pleural fluid, pericardial fluid, bronchoalveolar lavage fluid, sputum after liquifaction with N-acetylcysteine), direct testing of the sample is possible where the biological sample is dispensed into wells with a growth medium, and sample growth unit 760 may be optional.

System 700 may optionally include a subculture unit 770. Subculture unit 770 may be configured to perform a Gram stain and plate the blood culture broth to isolate colonies. Microorganisms from isolated colonies may be added to a well plate by dispensing unit 710. As explained above, embodiments of the present invention may exclude subculture unit 770.

IV. Example Methods

Embodiments of the present invention may include methods to test for antimicrobial susceptibility. Embodiments include using imaging techniques similar to those used by a commercially available flatbed scanner. The methods described herein can determine a susceptibility for a microorganism for a certain concentration of an antimicrobial. Methods may determine the MIC for a microorganism and antimicrobial. The MIC may be determined in 3 hours or less, including 1.5 hours or less, 1 hour or less, or 0.5 hours or less. Time to determine MIC may be improved with machine learning.

A. Determining Antimicrobial Susceptibility

FIG. 8 may include a method 800 for testing antimicrobial susceptibility. The method may include using any system described herein, including system 700 and subsystem 705.

At block 810, an image data set generated from imaging a plurality of wells may be received by a computer system. The plurality of well may include a first subset of wells containing a microorganism and a first initial concentration of an antimicrobial. The microorganism may be any microorganism described herein, including any pathogen. The plurality of wells may include a second subset of wells containing the microorganism and a second initial concentration of the antimicrobial. The microorganism concentration may be equal in the two subsets of wells. The concentration of the microorganism may be from $10^0$ to $10^{10}$ per ml, including from $10^4$ to $10^8$ per ml. Each well may further include signal amplifier, a pH indicator, or a dye indicative of metabolism. A subset of wells may include only one well or may include multiple wells. The subset of wells may include from 5 to 15 wells, including from 5 to 10 wells or from 10 to 15 wells.

The second initial concentration may be greater than the first initial concentration. The first initial concentration may be a doubling dilution of the second initial concentration. The second initial concentration may be equal to the first initial concentration multiplied by $2^n$, where n is a non-zero integer.

The plurality of wells may further include a third subset of wells containing the microorganism and a third initial concentration of the antimicrobial. The third initial concentration may be equal to the first initial concentration multiplied by $2^m$, where m is a non-zero integer and m does not equal n. Additional subsets of wells and additional initial concentrations of the antimicrobial may be included in the plurality of wells to correspond to multiple doubling dilutions. For example, there may be 10 to 16 initial concentrations of the antimicrobial in the plurality of wells.

The plurality of wells may include a well or wells containing the microorganism and excluding the antimicrobial. These wells may be a positive control to confirm growth in the microorganism. The plurality of wells may include a well or wells containing the antimicrobial and excluding the microorganism, which may be negative controls. The positive controls and/or the negative controls may be used for normalizing pixel intensities of other wells.

The image data set may be generated by measuring light from a light source reflected by each well of the plurality of wells. The image data set may include a value for pixel intensity for each pixel of a plurality of pixels. The pixel size may be less than or equal to 20 times the microorganism size, including less than or equal to 10 times, 5 times, or 2 times the microorganism size. The microorganism size may be the longest dimension of the microorganism or the diameter of the microorganism if the microorganism occupied a circle with the same area as the non-circular microorganism.

Measuring the light form the light source may include using a charge-coupled device, a contact image sensor, or photomultiplier tube. Measuring light from the light source may include using the charge-coupled device, and the image data set may be generated by moving the light source and the charge-coupled device relative the plurality of wells. The image data set may be generated using imaging unit 730, including a flatbed scanner.

In some embodiments, method 800 may include adding a microorganism to each well of the plurality of wells. The microorganism may be from any biological sample described herein. The microorganism may not have been isolated in a subculture. For example, the microorganism may have undergone growth in sample growth unit 760 but then underwent subculture in subculture unit 770 to isolate colonies. The microorganism may be added with a cell or cells. For example, if the microorganism is a virus, the virus may be added with a cell or within a cell.

Method 800 may include adding, by the automated dispenser, the first initial concentration of the antimicrobial to the first subset of wells. Method 800 may also include adding, by the automated dispenser, the second initial concentration of the antimicrobial to the second subset of wells. Method 800 may further include incubating the plurality of wells for a duration. Incubating the wells may be from 30 minutes to 4 hours, including from 30 minutes to 1 hour, from 1 to 1.5 hours, from 1.5 to 2 hours, from 2 to 3 hours, or from 3 to 4 hours.

At block 820, the image data set may be analyzed by the computer system to determine a first value of an image characteristic for the first subset of wells. The image characteristic may be a statistical measure of pixel intensities corresponding to a subset of wells. The statistical measure may be an average (e.g., mean, median, mode) or percentile pixel intensity. The image characteristic may be of pixel intensities of pixels corresponding to a central portion of each well of the subset of wells. The pixels in the central portion may exclude pixels that correspond to sidewalls of wells, shadowing of wells, or distortions/artifacts (e.g. parallax, lens flare). A model may determine the pixels corresponding to the central portion of the respective well.

The first value of the image characteristic may be adjusted for non-uniformities of the reflected light based on a location of each well in the first subset of wells. In some embodiments, the first value of the image characteristic may be a normalized or adjusted based on a control or based on image data from previously imaging the plurality of wells.

At block 830, the image data set may be analyzed by the computer system to determine a second value of the image characteristic for the second subset of wells. The second value may be similar to the first value, but determined for the second subset of wells.

At block 840, a classification of the resistance of the microorganism to the antimicrobial may be determined using at least one of the first value or the second value. The classification of the resistance of the microorganism to the antimicrobial may include an MIC, a likelihood of resistance, or a determination of resistant, not resistant (i.e., susceptible), or intermediately resistant.

The first value may be compared to the second value to determine a separation value. The separation value may be a difference or ratio of the first value and the second value. The separation value may be compared to a cutoff value. Determining the classification of the resistance may include determining that the microorganism is resistant to the first initial concentration of the antimicrobial when the separation value exceeds the cutoff value. In some cases, determining the microorganism is resistant to the first initial concentration includes determining that the first value is greater than a threshold value.

The second initial concentration may be the MIC when the second initial concentration is less than or equal to two times the first initial concentration when the separation value exceeds the cutoff value. The second value may be less than a certain threshold value. The MIC may be determined after incubating for 90 minutes or less, or any duration described herein.

The first value may be compared to a threshold value. When the first value exceeds the threshold value, the microorganism may be determined to be resistant to the first initial concentration of the antimicrobial. In some embodiments, the separation value does not need to be determined to determine the classification of the resistance. For example, a higher value may reflect a higher and darker pixel intensity, which may result from growth of the microorganism.

Based on the determined classification of the resistance, a patient having the microorganism may be treated with a dose of the antimicrobial based on at least one of the first initial concentration or the second initial concentration. If the microorganism was determined to be susceptible to either the first initial concentration or the second initial concentration, the patient may receive a treatment with the antimicrobial. The dose may be related to the initial concentration by a linear or non-linear equation. The initial concentration may be compared to a table to determine whether the microorganism is clinically resistant to the antimicrobial. For example, there are standards organizations (e.g., CLSI) that determine the relationship between MIC and clinical resistance and publish conversion tables for looking up the microorganism and antimicrobial and seeing if an MIC is susceptible, resistant, or intermediate. In some cases if the microorganism is determined to be resistant to the antimicrobial, the patient may be treated be treated with an alternative antimicrobial to which the microorganism is susceptible.

B. Determining MIC Using a Model

FIG. 9 shows a method 900 for testing antimicrobial susceptibility using a model, including a machine learning model.

At block 910, an input data structure may be received. The input data structure may include an input image data set comprising a value for pixel intensity for each pixel of a sample plurality of pixels. The image data set may be generated from imaging a sample plurality of wells. The image data set may be generated by any method and using any system described herein. The sample plurality of wells may contain a sample microorganism and a plurality of initial concentrations of a sample antimicrobial. The plurality of initial concentrations may be concentrations resulting from doubling dilutions of the sample antimicrobial. In some embodiments, the input data structure may further include a sample duration of incubating the sample microorganism.

At block 920, the input data structure may be inputted into a model. Blocks 930, 940, and 950 include elements of the training.

At block 930, a first plurality of first data structures may be received. Each first data structure of the first plurality of first data structures may include a first image data set comprising a value for pixel intensity for each pixel of a first plurality of pixels. The first image data set may be generated from imaging a first plurality of wells. The first plurality of wells may contain a first microorganism and the plurality of initial concentrations of a first antimicrobial. The first microorganism may have a known minimum inhibitory concentration to the first antimicrobial.

The first antimicrobial may or may not be the same antimicrobial as the sample antimicrobial. In some embodiments, a certain antimicrobial may be used to predict susceptibility for other antimicrobials. For example, cefazolin may be used to predict susceptibility to other cephalosporins for Enterobacteriaceae. The first microorganism may be the same or different as the sample microorganism. For example, all species of Enterobactericeae may behave similarly in response to an antibiotic, and therefore, training on one species may apply to other species.

Each first data structure may also include a first map representing the first plurality of wells with values indicating the initial concentration of the first antimicrobial for each well. The map may be a matrix or 2D array. In some embodiments, the map may not be rectangular. For example, the well plate may not be rectangular or not every well in well plate is measured.

In some embodiments, each first data structure may include a first duration of incubating the first microorganism. These first durations may allow for the model to determine the MIC in an image from a shorter duration when the MIC is more clearly determined from longer durations (e.g., FIG. 6).

At block 940, a plurality of first training samples is stored. Each first training sample may include one of the first plurality of first data structures and a first label indicating the known minimum inhibitory concentration of the first microorganism to the first antimicrobial.

At block 950, parameters of the model may be optimized, using the plurality of first training samples, based on outputs of the model matching or not matching corresponding labels of the first labels when the first plurality of first data structures is input to the model. The output of the model specifies the MIC of the first microorganism to the first antimicrobial for a given first data structure.

At block 960, the MIC of the sample microorganism to the sample antimicrobial may be determined using the model. A patient may be treated based on the MIC. The patient may be given a dose of the sample antimicrobial linearly or non-linearly related to the MIC.

The model may include a convolutional neural network (CNN). The CNN may include a set of convolutional filters configured to filter the first plurality of data structures and optionally the second plurality of data structures. The filter may be any filter described herein. The number of filters for each layer may be from 10 to 20, 20 to 30, 30 to 40, 40 to 50, 50 to 60, 60 to 70, 70 to 80, 80 to 90, 90 to 100, 100 to 150, 150 to 200, or more. The kernel size for the filters can be 2, 3, 4, 5, 6, 7, 8, 9, 10, 11, 12, 13, 14, 15, from 15 to 20, from 20 to 30, from 30 to 40, or more. The CNN may include an input layer configured to receive the filtered first plurality of data structures and optionally the filtered second plurality of data structures. The CNN may also include a plurality of hidden layers including a plurality of nodes. The first layer of the plurality of hidden layers coupled to the input layer. The CNN may further include an output layer coupled to a last layer of the plurality of hidden layers and configured to output an output data structure. The output data structure may include the properties.

The model may include a supervised learning model. Supervised learning models may include different approaches and algorithms including analytical learning, artificial neural network, backpropagation, boosting (meta-algorithm), Bayesian statistics, case-based reasoning, decision tree learning, inductive logic programming, Gaussian process regression, genetic programming, group method of data handling, kernel estimators, learning automata, learning classifier systems, minimum message length (decision trees, decision graphs, etc.), multilinear subspace learning, naive Bayes classifier, maximum entropy classifier, conditional random field, Nearest Neighbor Algorithm, probably approximately correct learning (PAC) learning, ripple down rules, a knowledge acquisition methodology, symbolic machine learning algorithms, sub symbolic machine learning algorithms, support vector machines, Minimum Complexity Machines (MCM), random forests, ensembles of classifiers, ordinal classification, data pre-processing, handling imbalanced datasets, statistical relational learning, or Proaftn, a multicriteria classification algorithm The model may include linear regression, logistic regression, deep recurrent neural network, Bayes classifier, hidden Markov model (HMM), linear discriminant analysis (LDA), k-means clustering, Density-based spatial clustering of applications with noise (DBSCAN), random forest algorithm, support vector machine (SVM), or any model described herein.

As part of training a machine learning model, the parameters of the machine learning model (such as weights, thresholds, e.g., as may be used for activation functions in neural networks, etc.) can be optimized based on the training samples (training set) to provide an optimized accuracy in classifying MIC, and/or susceptibility or resistance to one or many antimicrobials. Various form of optimization may be performed, e.g., backpropagation, empirical risk minimization, and structural risk minimization. A validation set of samples (data structure and label) can be used to validate the accuracy of the model. Cross-validation may be performed using various portions of the training set for training and validation. The model can comprise a plurality of submodels, thereby providing an ensemble model. The submodels may be weaker models that once combined provide a more accurate final model.

V. Example Logic and Computer Systems

Figure 10:
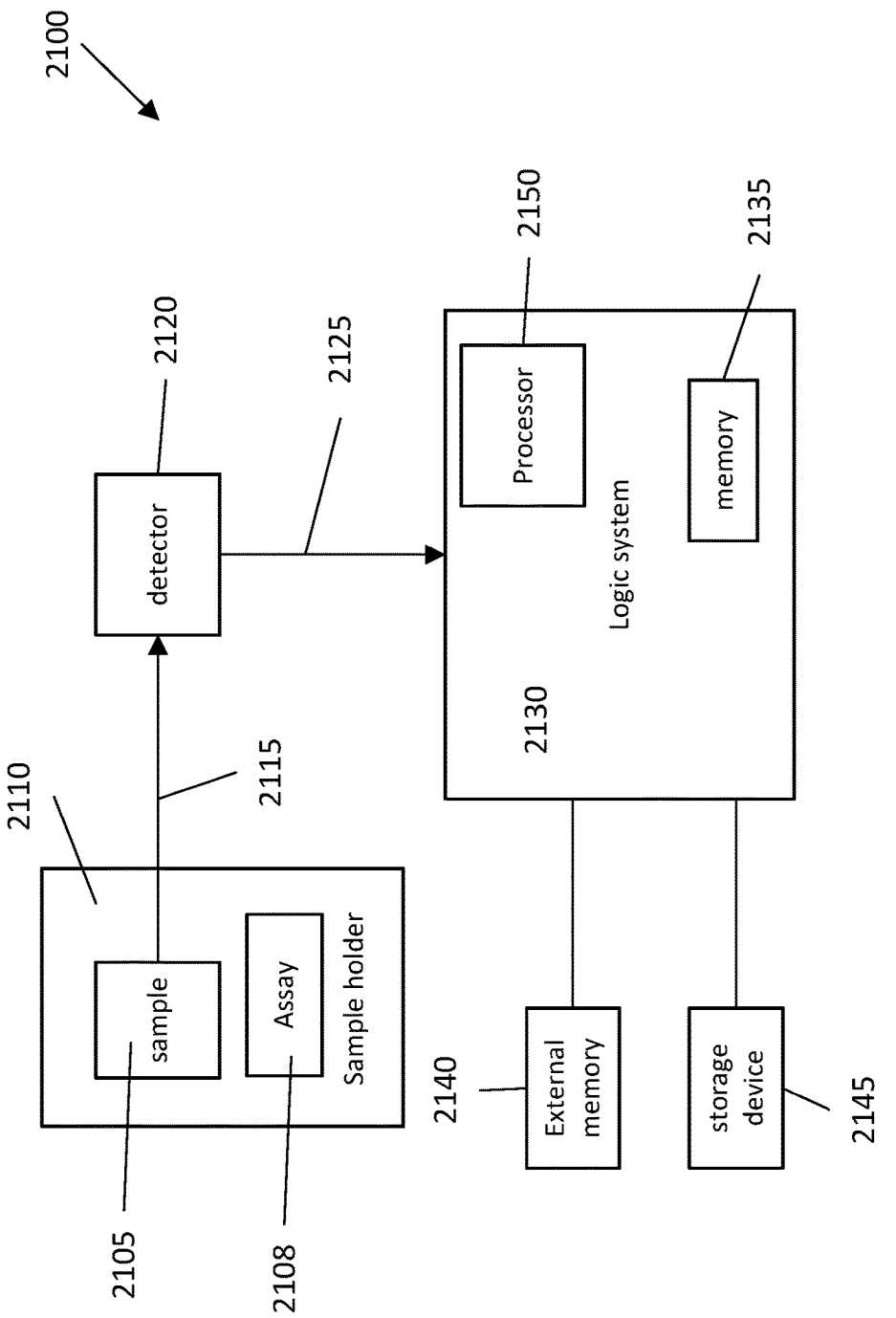
FIG. 10 shows a system according to embodiments of the present invention.

FIG. 10 illustrates a system 2100 according to an embodiment of the present invention. The system as shown includes a sample 2105, such as a microorganism within a sample holder 2110, where sample 2105 can be contacted with an assay 2108 to provide a signal of a light characteristic 2115. An example of a sample holder can be a well in a well plate. Light characteristic 2115 (e.g., an intensity, a wavelength), from the sample is detected by detector 2120. Detector 2120 can take a measurement at intervals (e.g., periodic intervals) to obtain data points that make up a data signal. Detector 2120 may be any sensor described herein. Sample holder 2110 and detector 2120 can form an assay device, e.g., an imaging unit according to embodiments described herein. A data signal 2125 is sent from detector 2120 to logic system 2130. Data signal 2125 may be stored in a local memory 2135, an external memory 2140, or a storage device 2145.

Logic system 2130 may be, or may include, a computer system, ASIC, microprocessor, etc. It may also include or be coupled with a display (e.g., monitor, LED display, etc.) and a user input device (e.g., mouse, keyboard, buttons, etc.). Logic system 2130 and the other components may be part of a stand-alone or network connected computer system, or they may be directly attached to or incorporated in a device (e.g., an imaging device) that includes detector 2120 and/or sample holder 2110. Logic system 2130 may also include software that executes in a processor 2150. Logic system 2130 may include a computer readable medium storing instructions for controlling system 2100 to perform any of the methods described herein. For example, logic system 2130 can provide commands to a system that includes sample holder 2110 such that dispensing, imaging, or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay.

Any of the computer systems mentioned herein may utilize any suitable number of subsystems. Examples of such subsystems are shown in FIG. 11 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones, other mobile devices, and cloud-based systems.

Figure 11:
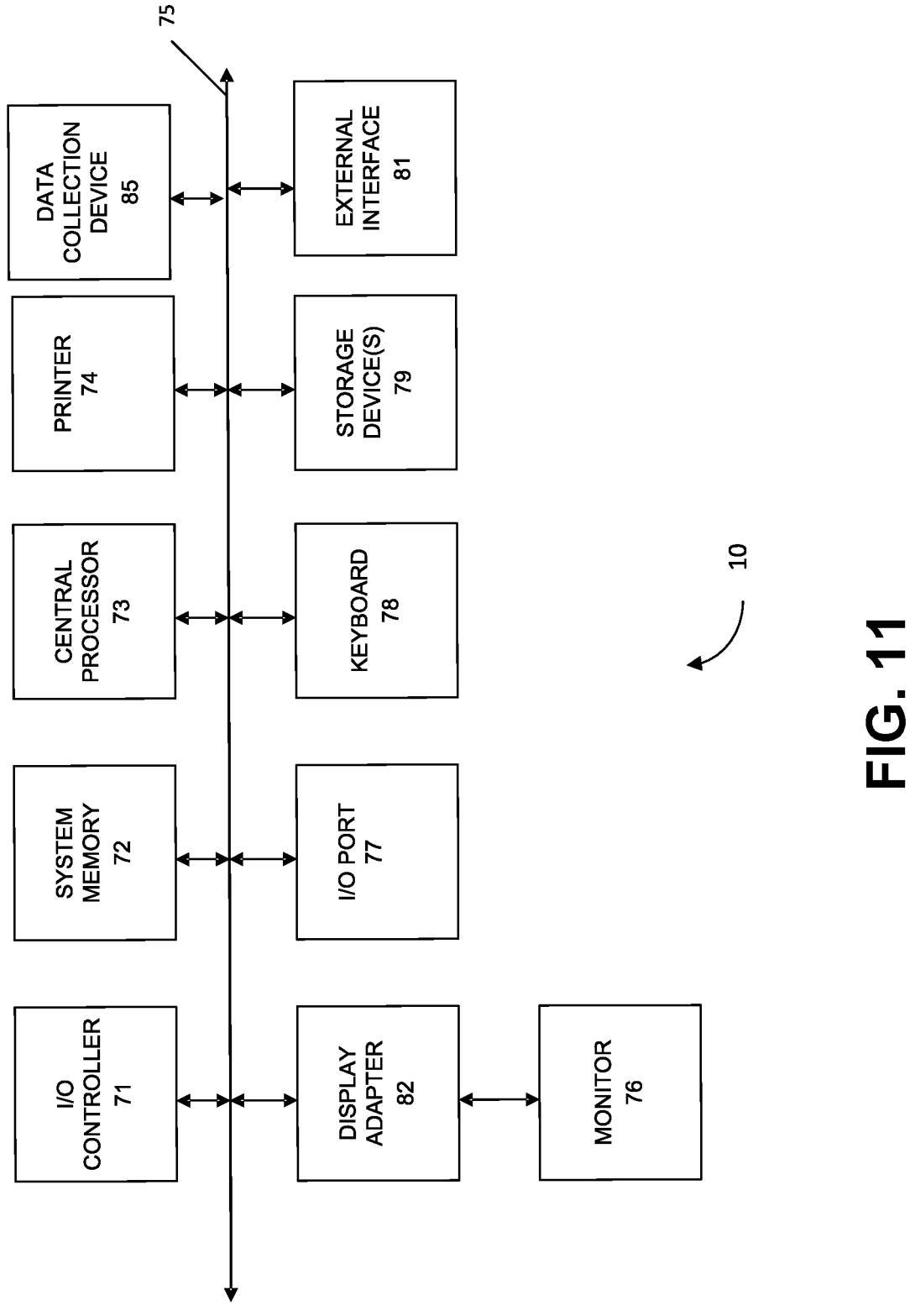
FIG. 11 shows a computer system according to embodiments of the present invention.

The subsystems shown in FIG. 11 are interconnected via a system bus 75. Additional subsystems such as a printer 74, keyboard 78, storage device(s) 79, monitor 76 (e.g., a display screen, such as an LED), which is coupled to display adapter 82, and others are shown. Peripherals and input/output (I/O) devices, which couple to I/O controller 71, can be connected to the computer system by any number of means known in the art such as input/output (I/O) port 77 (e.g., USB). For example, I/O port 77 or external interface 81 (e.g. Ethernet, Wi-Fi, Bluetooth, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk)

or Blu-ray disk, flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the present disclosure has been presented for the purposes of illustration and description. It is not intended to be exhaustive or to limit the disclosure to the precise form described, and many modifications and variations are possible in light of the teaching above.

A recitation of "a", "an", or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

All patents, patent applications, publications, and descriptions mentioned herein are incorporated by reference in their entirety for all purposes. None is admitted to be prior art.

What is claimed is:

1. A method for testing antimicrobial susceptibility, the method comprising:
   receiving, by a computer system, an image data set generated from imaging a plurality of wells at one or more time points after incubation using an imaging unit comprising a charge-coupled device (CCD) sensor, a contact image sensor (CIS), or other sensor that uses photodiodes, wherein:

the plurality of wells comprises a first subset of wells containing a microorganism and a first initial concentration of an antimicrobial, the plurality of wells comprises a second subset of wells containing the microorganism and a second initial concentration of an antimicrobial, the second initial concentration being greater than the first initial concentration, the image data set is generated by measuring light from a light source reflected by each well of the plurality of wells at the one or more time points, and the image data set comprises a value for pixel intensity for each pixel of a plurality of pixels at each time point of the one or more time points;

generating, by the computer system, an input data structure comprising the image data set;

analyzing, by the computer system, the image data set to determine a first value of an image characteristic at a first time point of the one or more time points for the first subset of wells, the image characteristic being a statistical measure of pixel intensities corresponding to the first subset of wells, wherein the analyzing comprises inputting the input data structure to a trained model to generate the first value of the image characteristic;

analyzing, by the computer system, the image data set to determine a second value of the image characteristic at the first time point of the one or more time points for the second subset of wells, the image characteristic being a statistical measure of pixel intensities corresponding to the second subset of wells, wherein the analyzing comprises inputting the input data structure to the trained model to generate the second value of the image characteristic; and determining a classification of a resistance of the microorganism to the antimicrobial using at least one of the first value or the second value.

2. The method of claim 1, wherein the first subset of wells and the second subset of wells are arranged on a well plate based on a particular platemap, and wherein the analyzing further comprises correcting a variability caused by a location of each well on the particular platemap before generating the first value and the second value.

3. The method of claim 1, further comprising:

adding the microorganism to each well of the plurality of wells;

adding, by an automated dispenser, the first initial concentration of the antimicrobial to the first subset of wells;

adding, by the automated dispenser, the second initial concentration of the antimicrobial to the second subset of wells; and incubating the plurality of wells for a duration of less than 90 minutes before generating the image data set.

4. The method of claim 1, wherein the second initial concentration is equal to the first initial concentration multiplied by $2^n$, where n is a non-zero integer.

5. The method of claim 4, wherein:

the plurality of wells further comprises a third subset of wells containing the microorganism and a third initial concentration of the antimicrobial, the third initial concentration is equal to the first initial concentration multiplied by $2^m$, where m is a non-zero integer and m does not equal n.

6. The method of claim 1, further comprising:

comparing the first value to the second value to determine a separation value, comparing the separation value to a cutoff value, wherein determining the classification of the resistance comprises:

determining that the microorganism is resistant to the first initial concentration of the antimicrobial when the separation value exceeds the cutoff value.

7. The method of claim 6, further comprising:

determining a minimum inhibitory concentration to be the second initial concentration when the second initial concentration is less than or equal to two times the first initial concentration.

8. The method of claim 1, wherein the statistical measure of pixel intensities corresponds to a central portion of each well of each subset of wells, wherein the central portion of each well excludes pixels corresponding to a sidewall of the well or a shadow of the sidewall.

9. The method of claim 1, further comprising:

comparing the first value to a threshold value, wherein determining the classification of the resistance comprises:

determining the microorganism is resistant to the first initial concentration of the antimicrobial when the first value exceeds the threshold value.

10. The method of claim 1, wherein the imaging unit is a flatbed scanner.

11. The method of claim 1, wherein:

measuring light from the light source comprises using the imaging unit comprising the CCD sensor, the image data set is generated by:

moving the light source and the imaging unit relative to the plurality of wells.

12. The method of claim 1, further comprising analyzing, by the computer system, the image data set to determine (i) a third value of the image characteristic at a second point of the one or more time points for the first subset of wells and (ii) a fourth value of the image characteristic at the second point of the one or more time points for the second subset of wells, wherein the classification of the resistance of the microorganism to the antimicrobial is determined based on the first value, the second value, the third value, and the fourth value.

13. The method of claim 8, wherein the statistical measure is selected from the group consisting of mean, median, mode, and percentile of pixel intensities of pixels corresponding to the central portion of each well of each subset of wells.

14. The method of claim 1, wherein:

the first value of an image characteristic for the first subset of wells is adjusted for non-uniformities of the reflected light based on a location of each well in the first subset of wells.

15. The method of claim 1, wherein the classification of the resistance of the microorganism to the antimicrobial comprises a minimum inhibitory concentration, a likelihood of resistance, or a determination of resistant or not resistant.

16. The method of claim 1, wherein:

the first subset of wells comprises multiple wells, and the image characteristic is an average pixel intensity corresponding to the wells.

17. The method of claim 1, wherein the plurality of wells comprises a well containing the microorganism and excluding the antimicrobial.

18. The method of claim 1, wherein:

each pixel of the plurality of pixels is characterized by a pixel size, the microorganism is characterized by a microorganism size, and the pixel size is less than or equal to 20 times the microorganism size.

19. The method of claim 1, wherein the microorganism has not been isolated in a subculture.

20. The method of claim 1, further comprising treating a patient having the microorganism with a dose of the antimicrobial based on at least one of the first initial concentration or the second initial concentration.

21. A method for testing antimicrobial susceptibility, the method comprising:

receiving an input data structure, the input data structure comprising:

an input image data set comprising a value for pixel intensity for each pixel of a sample plurality of pixels, the input image data set generated from imaging a sample plurality of wells at one or more time points after incubation using an imaging unit comprising a charge-coupled device (CCD) sensor, a contact image sensor (CIS), or other sensor that uses photodiodes, the sample plurality of wells containing a sample microorganism and a first and a second initial concentrations of a sample antimicrobial, the second initial concentration being greater than the first initial concentration, and a sample map representing the sample plurality of wells with values indicating an initial concentration of the sample antimicrobial in each well;

inputting the input data structure into a model, the model trained by:

receiving a first plurality of first data structures, each first data structure of the first plurality of first data structures comprising:

a first image data set comprising a value for pixel intensity for each pixel of a first plurality of pixels, the first image data set generated from imaging a first plurality of wells, the first plurality of wells containing a first microorganism and a plurality of initial concentrations of a first antimicrobial, the first microorganism having a known minimum inhibitory concentration to the first antimicrobial, and a first map representing the first plurality of wells with values indicating the initial concentration of the first antimicrobial for each well, storing a plurality of first training samples, each including one of the first plurality of first data structures and a first label indicating the known minimum inhibitory concentration of the first microorganism to the first antimicrobial, and optimizing, using the plurality of first training samples, parameters of the model based on outputs of the model matching or not matching corresponding labels of the first labels when the first plurality of first data structures is input to the model, wherein an output of the model specifies the minimum inhibitory concentration of the first microorganism to the first antimicrobial for a given first data structure; and determining, using the model, a minimum inhibitory concentration of the sample microorganism to the sample antimicrobial, wherein the determining comprises:

determining a first value of an image characteristic at a first time point of the one or more time points for a first subset of the sample plurality of wells, the image characteristic being a statistical measure of pixel intensities corresponding to the first subset, and determining a second value of the image characteristic at the first time point of the one or more time points for a second subset of the sample plurality of wells, the image characteristic being a statistical measure of pixel intensities corresponding to the second subset, wherein the minimum inhibitory concentration is determined using at least one of the first value or the second value.

22. The method of claim 21, wherein:

the input data structure further comprises a sample duration of incubating the sample microorganism, and each first data structure of the first plurality of first data structures further comprises a first duration of incubating the first microorganism.

23. The method of claim 21, wherein the plurality of initial concentrations comprises concentrations resulting from doubling dilutions of the sample antimicrobial.

24. A system for antimicrobial susceptibility testing, the system comprising:

a dispensing unit configured to automatically dispense a plurality of concentrations of an antimicrobial to a plurality of locations on a well plate;

an incubation unit configured to receive the well plate and to maintain a temperature set point;

an imaging unit comprising a light source and a charge-coupled device (CCD) sensor, a contact image sensor (CIS), or other sensor that uses photodiodes, the imaging unit configured to measure light from the light source reflected by the well plate and to generate an image data set from the measured light, wherein the image data set comprises a value for pixel intensity for each pixel of a plurality of pixels; and a processor configured to execute a plurality of instructions, the plurality of instructions comprising:

generating an input data structure comprising the image data set, analyzing the image data set to determine a first value of an image characteristic at a first time point of the one or more time points for a first subset of wells of the well plate, the first subset of wells containing a microorganism and a first concentration of the antimicrobial, the image characteristic is a statistical measure of pixel intensities corresponding to the first subset of wells, wherein the analyzing comprises inputting the input data structure to a trained model to generate the first value of the image characteristic, analyzing the image data set to determine a second value of the image characteristic at the first time point of the one or more time points for a second subset of wells of the well plate, the second subset of wells containing the microorganism and a second concentration of the antimicrobial, the second concentration being greater than the first concentration, the image characteristic being a statistical measure of pixel intensities corresponding to the second subset of wells, wherein the analyzing comprises inputting the input data structure to the trained model to generate the second value of the image characteristic, and determining a classification of a resistance of the microorganism to the antimicrobial using the first value and the second value.

25. The system of claim 24, wherein the sensor has a resolution greater than or equal to 600 dpi.

26. The system of claim 24, wherein the well plate comprises 96 or more wells.

27. The system of claim 24, wherein the plurality of concentrations comprise serial dilutions of the antimicrobial.

28. The system of claim 24, wherein the dispensing unit is further configured to dispense a microorganism to the plurality of locations on the well plate.

29. The system of claim 24, wherein the imaging unit further comprises a well plate holder to immobilize the well plate.

30. The system of claim 24, wherein the light source comprises a fluorescent lamp or a xenon lamp.

31. The system of claim 24, wherein the light source comprises a cold cathode fluorescent lamp.

32. The system of claim 24, wherein:

the light source is configured to move, and the imaging unit further comprises a mirror to reflect light to the sensor during movement of the light source.

* * * * *